United States Patent
Scheib et al.

(10) Patent No.: US 10,779,832 B2
(45) Date of Patent: Sep. 22, 2020

(54) CIRCULAR ANVIL INTRODUCTION SYSTEM WITH ALIGNMENT FEATURE

(71) Applicant: Ethicon LLC, Guaynabo, PR (US)

(72) Inventors: Charles J. Scheib, Loveland, OH (US); Cortney E. Henderson, Wilmington, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 276 days.

(21) Appl. No.: 15/651,121

(22) Filed: Jul. 17, 2017

(65) Prior Publication Data

US 2018/0000484 A1    Jan. 4, 2018

Related U.S. Application Data

(63) Continuation of application No. 13/693,455, filed on Dec. 4, 2012, now Pat. No. 9,724,100.

(51) Int. Cl.
*A61B 17/115* (2006.01)
*A61B 17/11* (2006.01)
(Continued)

(52) U.S. Cl.
CPC ....... *A61B 17/1155* (2013.01); *A61B 17/1114* (2013.01); *A61B 2017/00473* (2013.01); *A61B 2017/07257* (2013.01)

(58) Field of Classification Search
CPC ...... A61B 17/1155; A61B 2017/07257; A61B 17/1114; A61B 2017/00473
(Continued)

(56) References Cited

U.S. PATENT DOCUMENTS 4,573,468 A * 3/1986 Conta ................ A61B 17/115
227/179.1
4,805,823 A   2/1989 Rothfuss
(Continued)

FOREIGN PATENT DOCUMENTS

CN    2331320 Y    8/1999
CN    2820097 Y    9/2006
(Continued)

OTHER PUBLICATIONS

Chinese Office Action, First, dated Dec. 2, 2016 for Application No. CN 201380063916.5, 7 pgs.
(Continued)

*Primary Examiner* — Robert F Long
(74) *Attorney, Agent, or Firm* — Frost Brown Todd LLC

(57) ABSTRACT

An apparatus is provided for stapling tissue. The apparatus includes an anvil and a trocar selectively coupled with the anvil. The anvil may have an inner opening and a plurality of staple pockets aligned around a surface of the anvil. The anvil may be inserted trans-orally through an esophagus prior to being coupled with the trocar. The trocar may include a shaft and a locking assembly. The locking assembly may secure the anvil in position relative to the trocar when the locking assembly is in the expanded position. The apparatus may also include an alignment assembly to align the staple pockets of the anvil relative to the apparatus. The apparatus may also include an introduction assembly to guide the anvil through the esophagus.

18 Claims, 31 Drawing Sheets

(51) Int. Cl.
*A61B 17/00* (2006.01)
*A61B 17/072* (2006.01)

(58) Field of Classification Search
USPC .......................................... 227/175.1–182.1
See application file for complete search history.

(56) References Cited

U.S. PATENT DOCUMENTS

| | | | |
|---|---|---|---|
| 5,197,648 A * | 3/1993 | Gingold | A61B 17/115 227/179.1 |
| 5,205,459 A * | 4/1993 | Brinkerhoff | A61B 17/115 227/179.1 |
| 5,271,543 A | 12/1993 | Grant et al. | |
| 5,271,544 A | 12/1993 | Fox et al. | |
| 5,275,322 A | 1/1994 | Brinkerhoff et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,368,215 A * | 11/1994 | Green | A61B 17/115 227/179.1 |
| 5,415,334 A | 5/1995 | Williamson, IV et al. | |
| 5,465,895 A | 11/1995 | Knodel et al. | |
| 5,533,661 A | 7/1996 | Main et al. | |
| 5,562,690 A * | 10/1996 | Green | A61B 17/11 606/151 |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,758,814 A * | 6/1998 | Gallagher | A61B 17/115 227/176.1 |
| 5,814,055 A | 9/1998 | Knodel et al. | |
| 5,860,581 A * | 1/1999 | Robertson | A61B 17/1114 227/179.1 |
| 6,050,472 A * | 4/2000 | Shibata | A61B 17/115 227/175.2 |
| 6,053,390 A * | 4/2000 | Green | A61B 17/115 227/179.1 |
| 6,258,107 B1 * | 7/2001 | Balazs | A61B 17/115 227/175.1 |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,122,044 B2 | 10/2006 | Bolduc et al. | |
| 7,143,923 B2 | 12/2006 | Shelton, IV et al. | |
| 7,144,409 B2 | 12/2006 | Aranyi | |
| 7,303,108 B2 | 12/2007 | Shelton, IV | |
| 7,364,060 B2 | 4/2008 | Milliman | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,422,138 B2 | 9/2008 | Bilotti et al. | |
| 7,434,715 B2 | 10/2008 | Shelton, IV et al. | |
| 7,721,930 B2 | 5/2010 | McKenna et al. | |
| 7,901,416 B2 * | 3/2011 | Nolan | A61B 17/1114 227/175.1 |
| 8,348,122 B2 | 1/2013 | Milliman et al. | |
| 8,613,383 B2 | 12/2013 | Beckman et al. | |
| 9,033,204 B2 | 5/2015 | Shelton, IV et al. | |
| 9,364,233 B2 | 6/2016 | Alexander, III et al. | |
| 9,522,005 B2 | 12/2016 | Williams et al. | |
| 9,724,100 B2 | 8/2017 | Scheib et al. | |
| 2005/0116009 A1 * | 6/2005 | Milliman | A61B 17/068 227/176.1 |
| 2006/0097025 A1 * | 5/2006 | Milliman | A61B 17/115 227/175.1 |
| 2007/0043387 A1 * | 2/2007 | Vargas | A61B 17/11 606/185 |
| 2007/0175963 A1 * | 8/2007 | Bilotti | A61B 17/115 227/179.1 |
| 2009/0001121 A1 * | 1/2009 | Hess | A61B 17/0644 227/175.1 |
| 2010/0038401 A1 * | 2/2010 | Milliman | A61B 17/1114 227/175.1 |
| 2011/0095067 A1 * | 4/2011 | Ohdaira | A61B 17/07207 227/175.2 |
| 2011/0257635 A1 * | 10/2011 | Whitman | A61B 10/0233 606/1 |
| 2012/0061447 A1 * | 3/2012 | Williams | A61B 17/115 227/175.1 |
| 2012/0234898 A1 * | 9/2012 | Shelton, IV | A61B 17/00234 227/179.1 |
| 2013/0175318 A1 * | 7/2013 | Felder | A61B 17/072 227/179.1 |
| 2015/0173755 A1 * | 6/2015 | Baxter, III | A61B 17/072 227/180.1 |
| 2017/0000487 A1 * | 1/2017 | Swayze | A61B 17/1155 |

FOREIGN PATENT DOCUMENTS

| | | |
|---|---|---|
| EP | 0 536 882 A2 | 4/1993 |
| EP | 0 570 915 A2 | 11/1993 |
| EP | 2 153 781 A2 | 2/2010 |
| EP | 2486859 A2 | 8/2012 |
| RU | 2025093 C1 | 12/1994 |
| WO | WO 2004/032766 A2 | 4/2004 |
| WO | WO 2005/037084 A2 | 4/2005 |
| WO | WO 2012/125615 A2 | 9/2012 |

OTHER PUBLICATIONS

Chinese Search Report dated Jan. 20, 2017 for Application No. CN 201380063916.5, 2 pgs.
Chinese Office Action, Second, dated Jul. 25, 2017 for Application CN 201380063916.5, 9 pgs.
International Search Report dated Mar. 5, 2015 for Application No. PCT/US2013/073106, 8 pgs.
International Preliminary Report on Patentability and Written Opinion dated Jun. 9, 2015 for Application No. PCT/US2013/073106, 9 pgs.
Japanese Office Action, Notification of Reasons for Refusal, dated Jun. 23, 2017 for Application No. JP 2015-545820, 9 pgs.
Japanese Office Action, Decision to Grant Patent, dated Dec. 6, 2017 for Application No. JP 2015-545820, 6 pgs.
Brazilian Office Action dated Dec. 6, 2019 for Application No. BR 112015013143-3, 3 pgs.
Indian Office Action, Examination Report, dated Sep. 24, 2019 for Application No. 3977/DELNP/2015, 5 pgs.
Mexican Office Action, 1$^{st}$ Substantive requirement, dated Feb. 28, 2018 for Application No. MX/a/2015/007041, 3 pgs.
Russian Office Action dated Dec. 12, 2017 for Application No. RU 2015126875/14, 2 pgs.

* cited by examiner

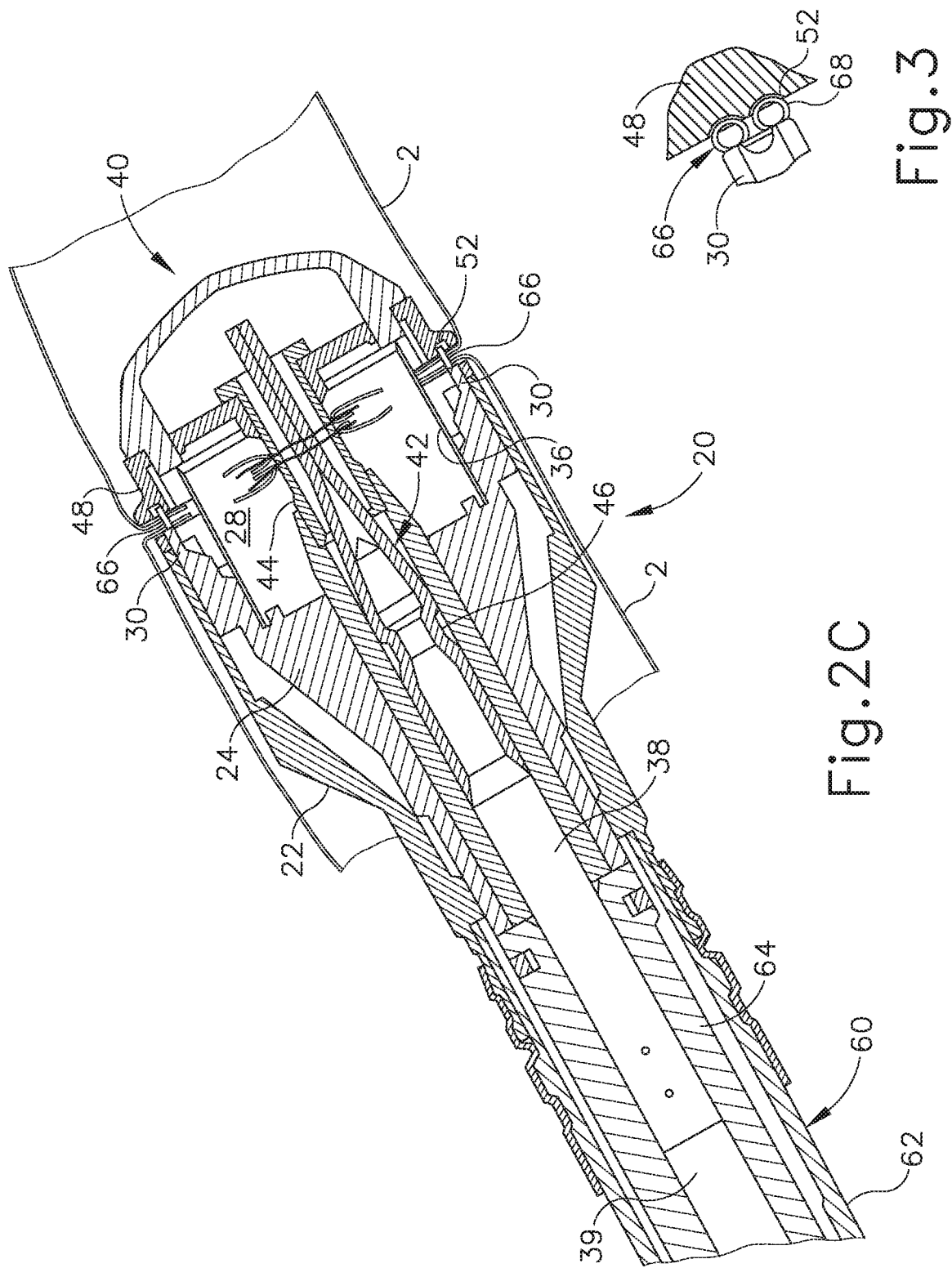

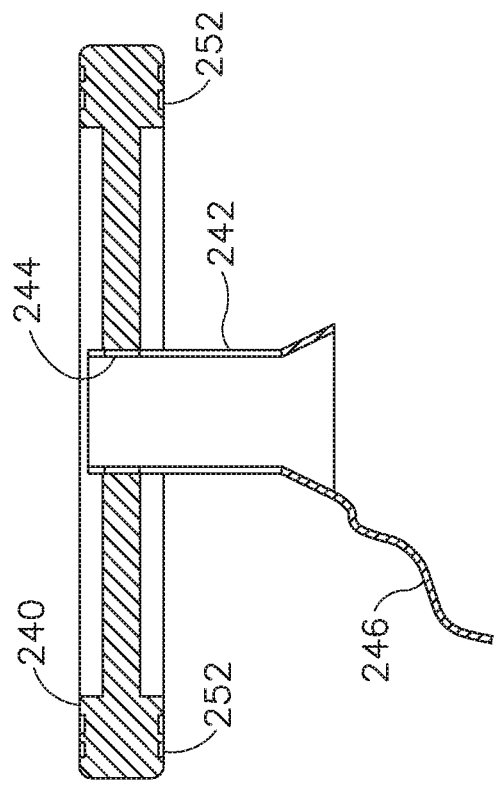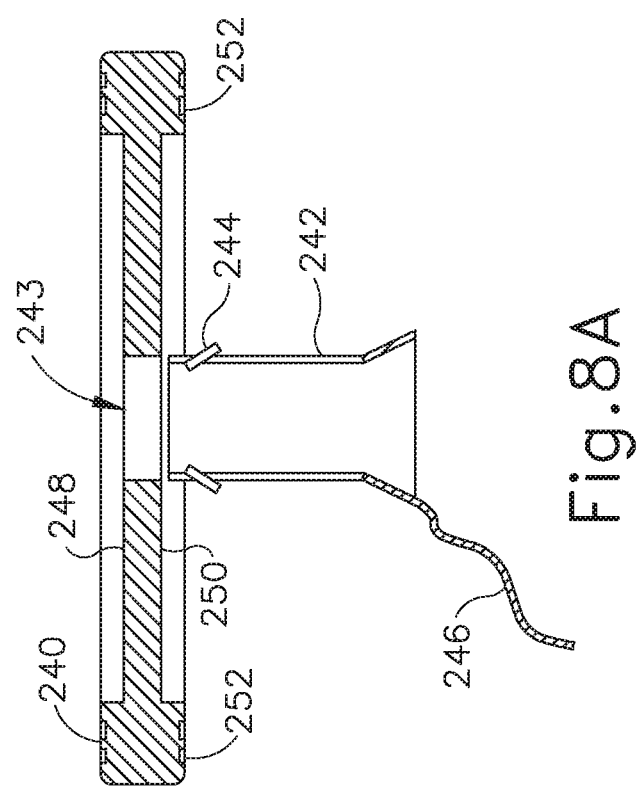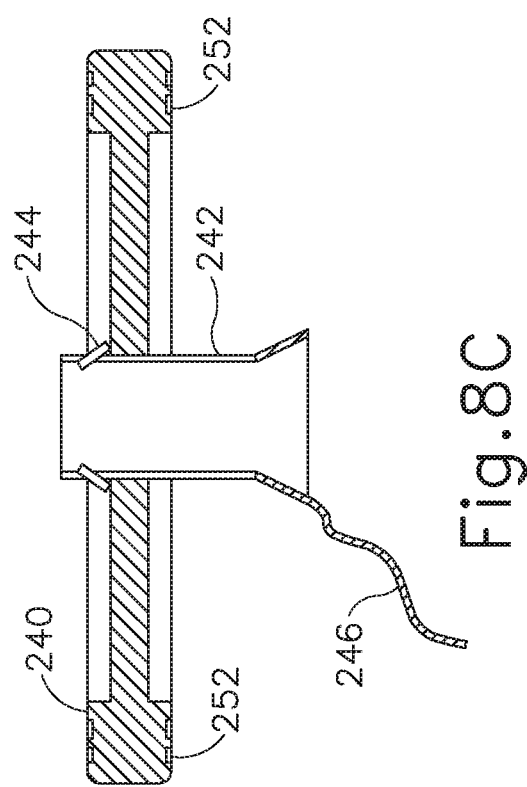

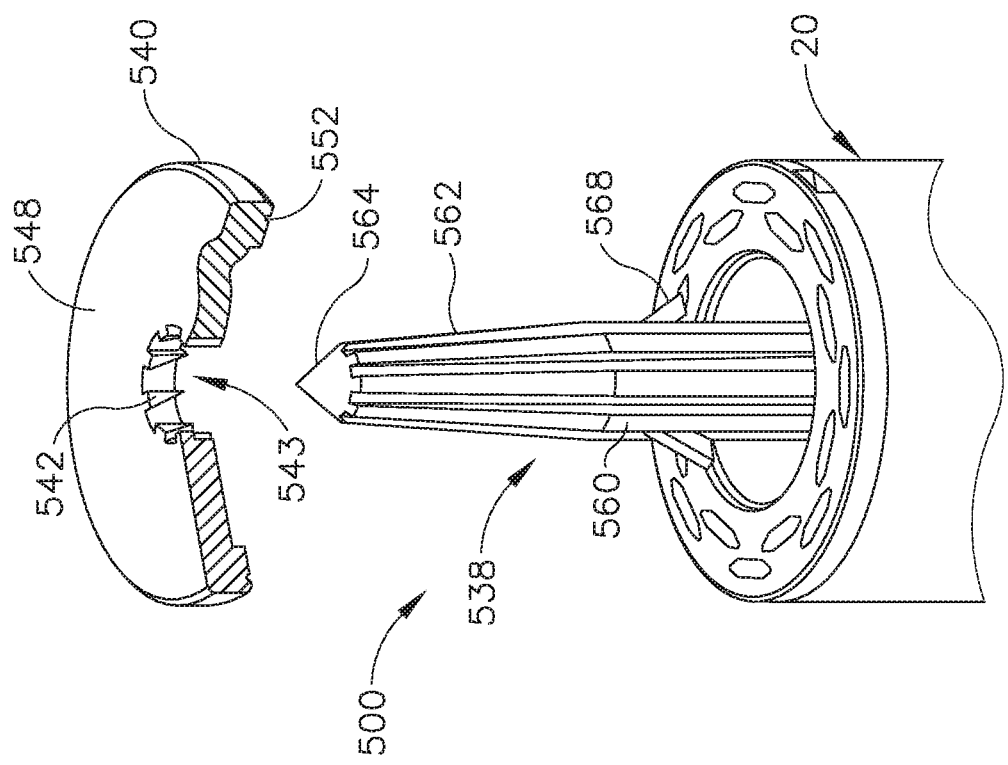
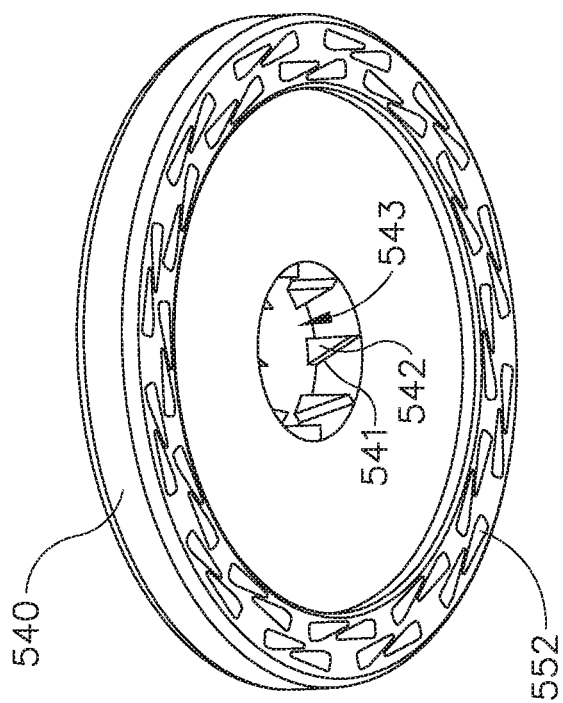
Fig. 15A
Fig. 14

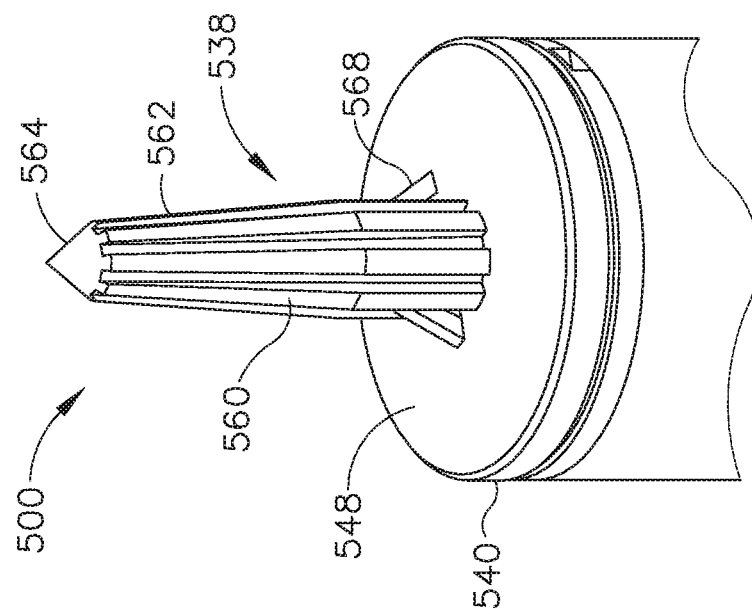
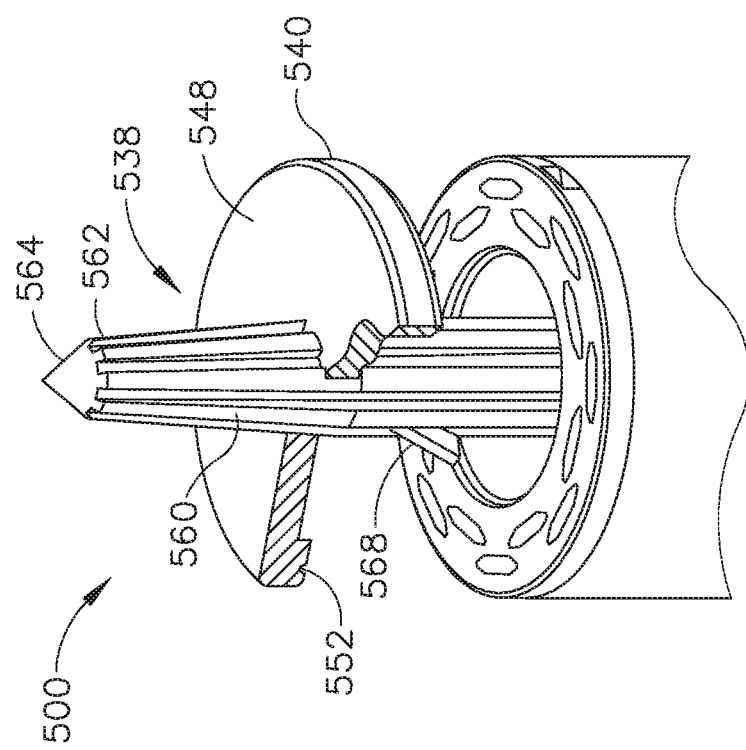
Fig. 15B
Fig. 15C

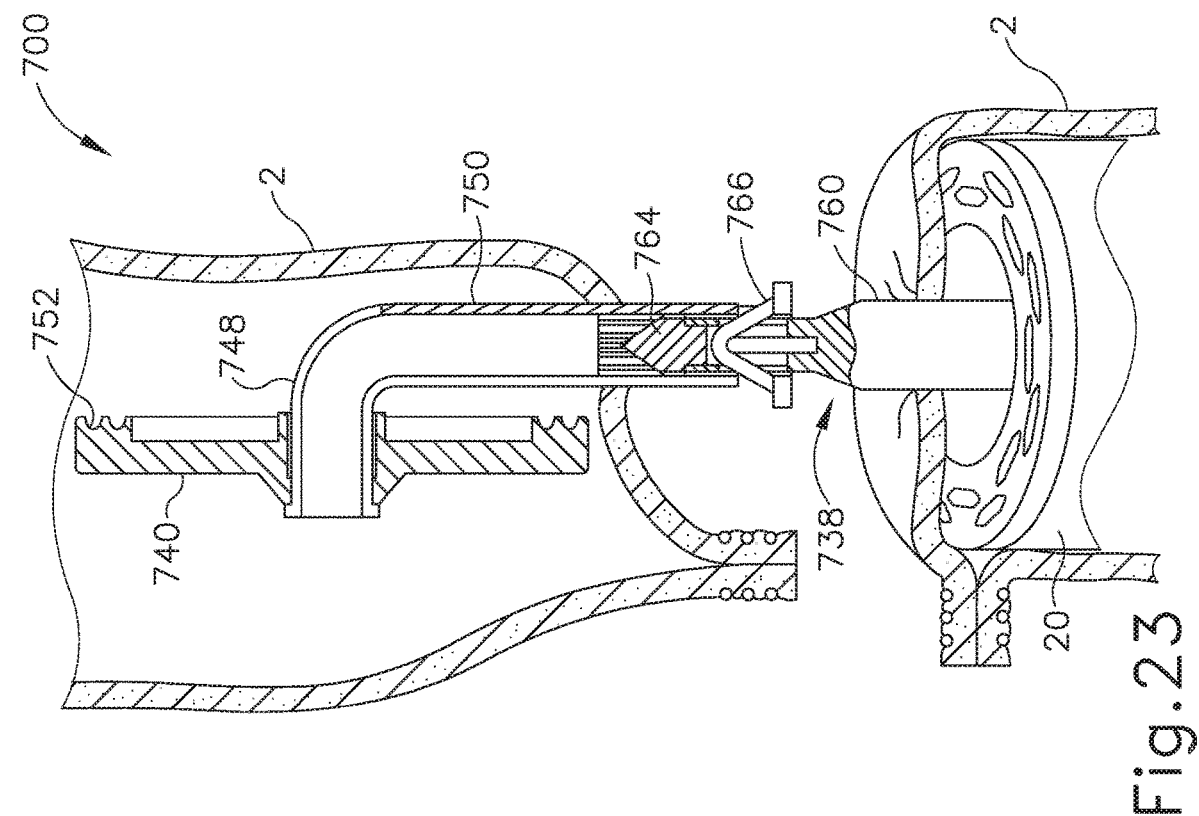
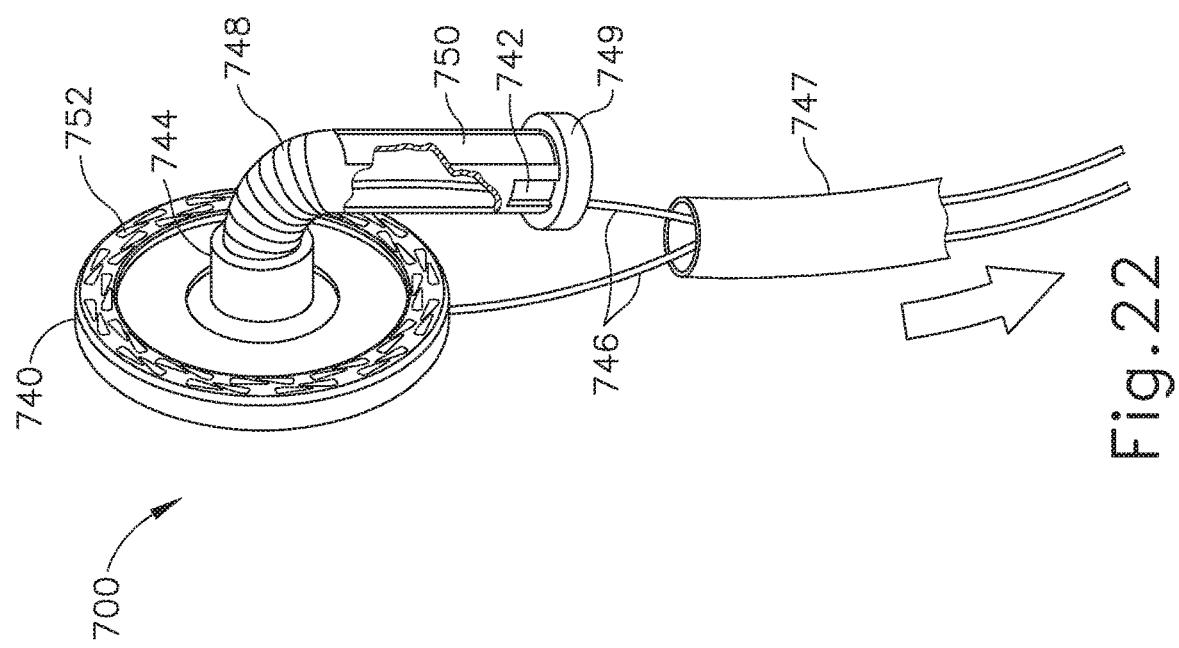
Fig. 22
Fig. 23

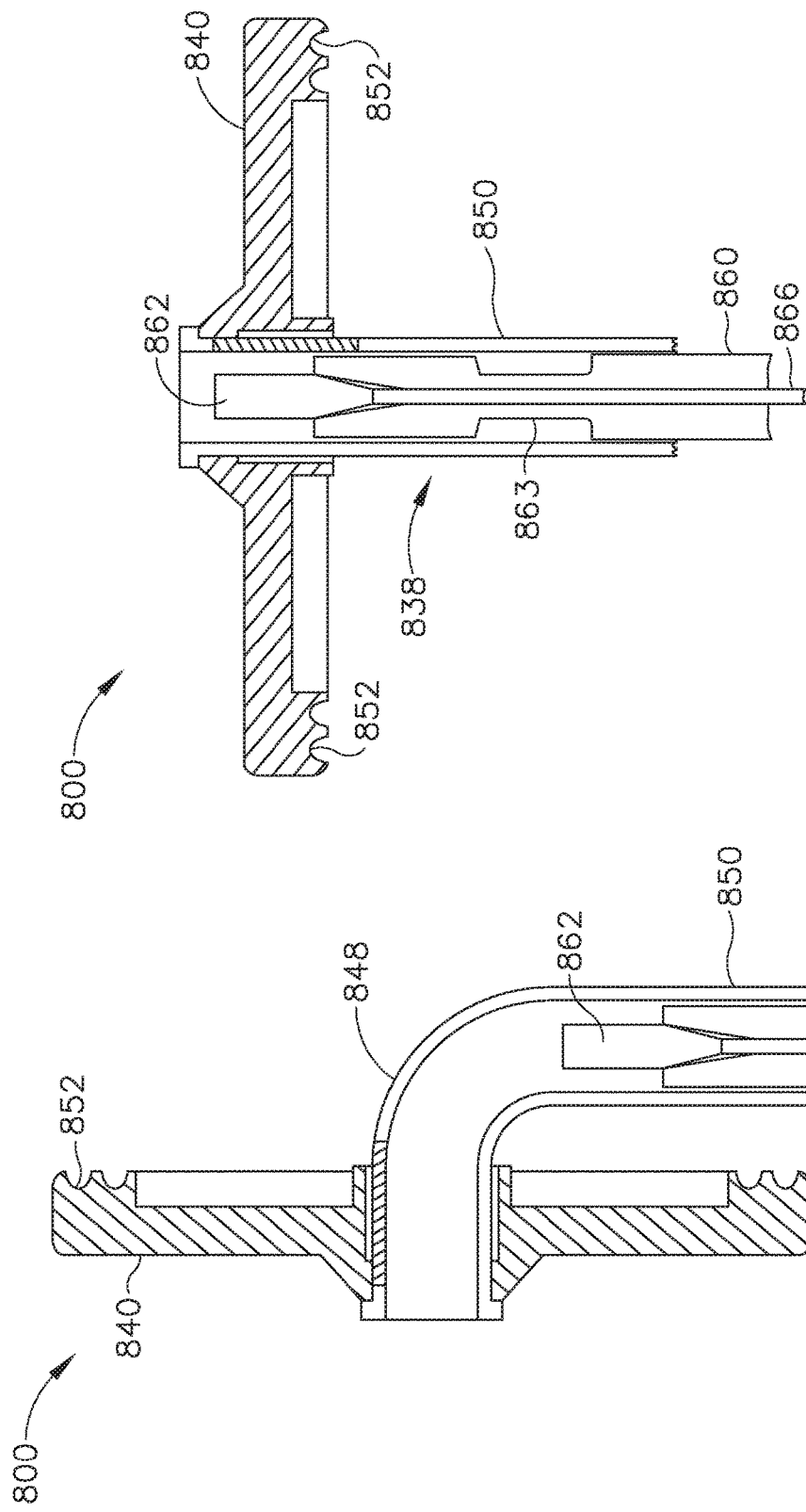

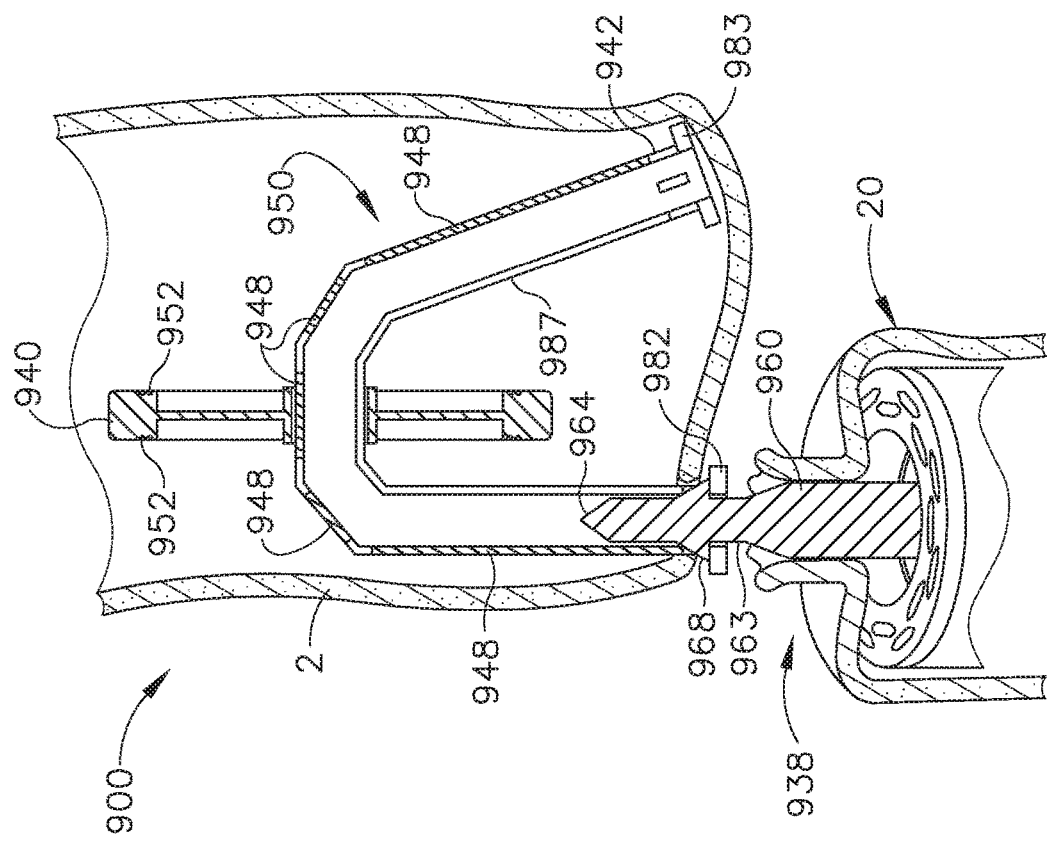
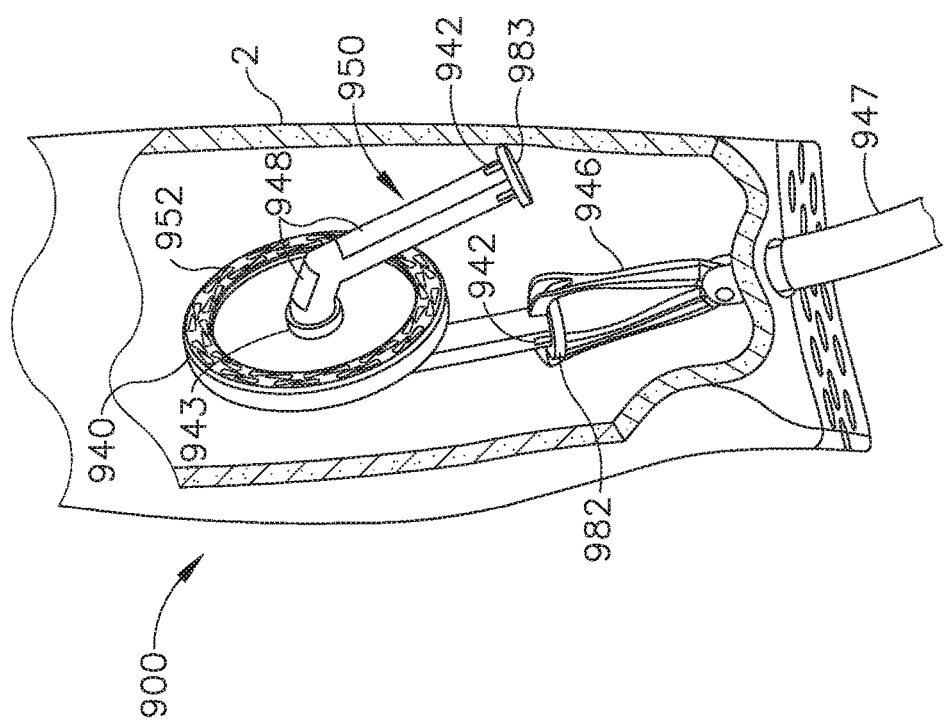

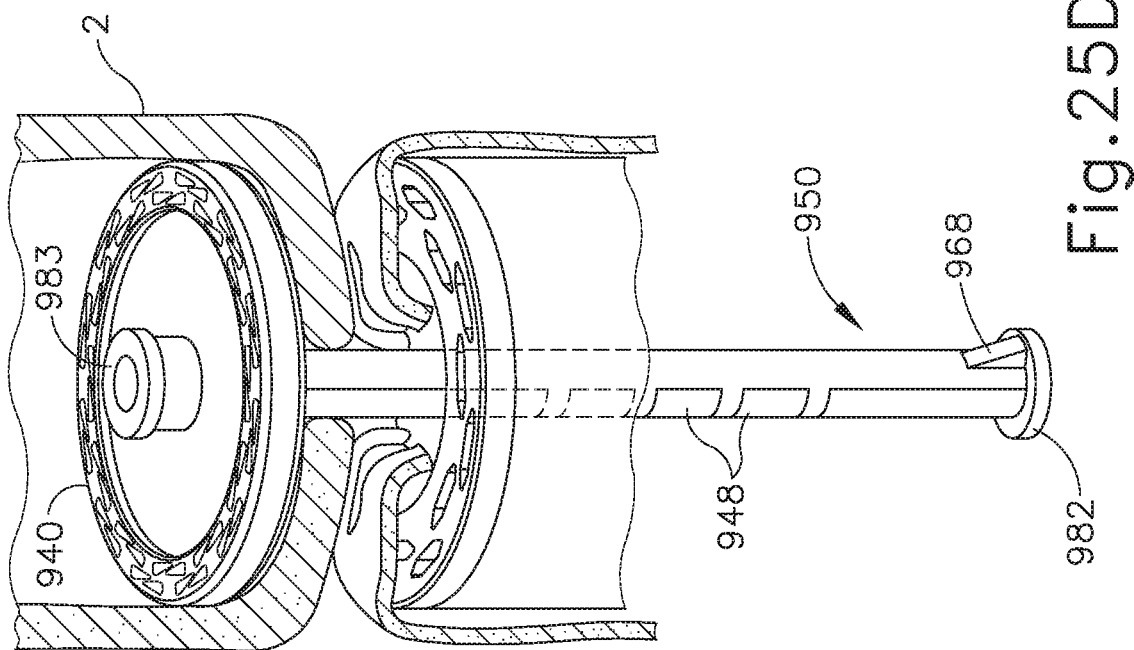
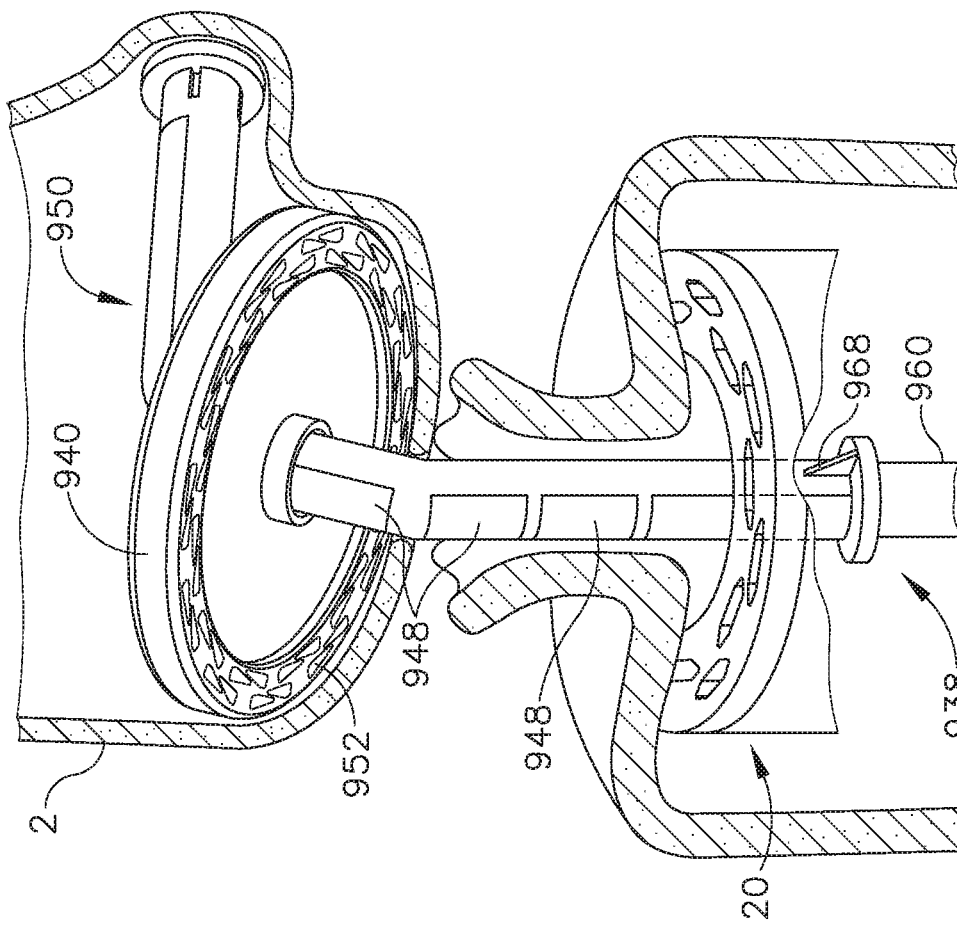

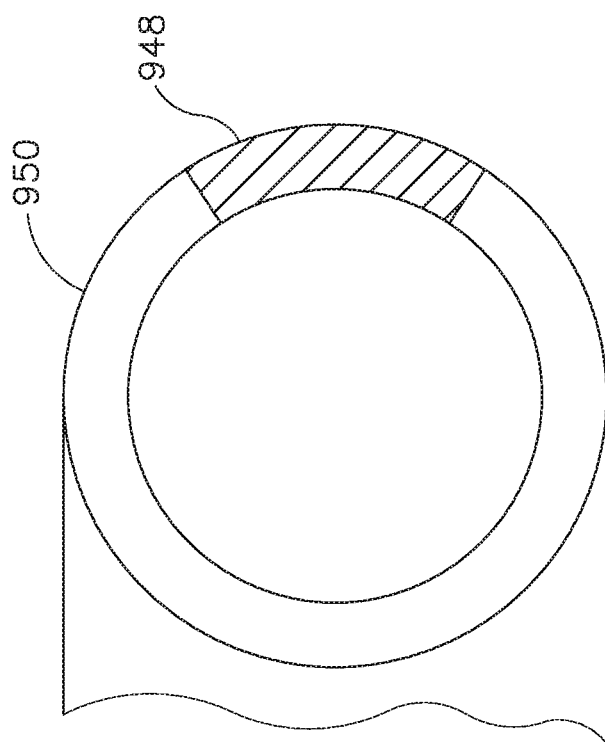
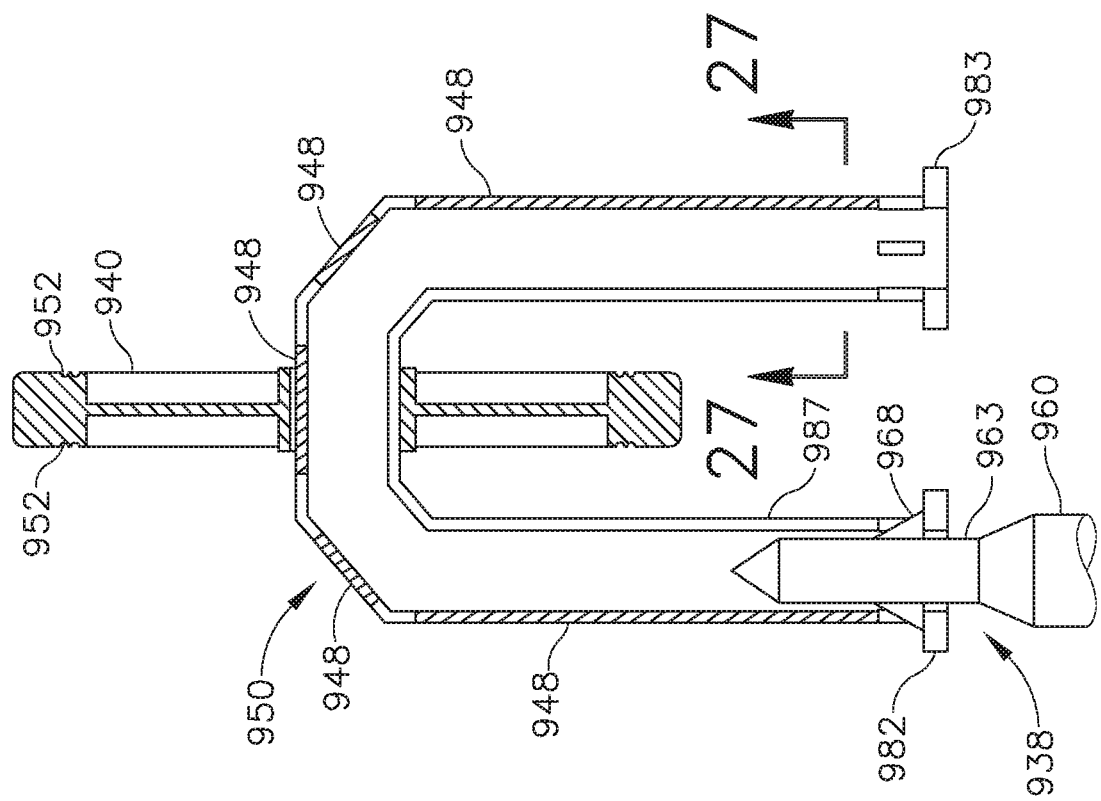

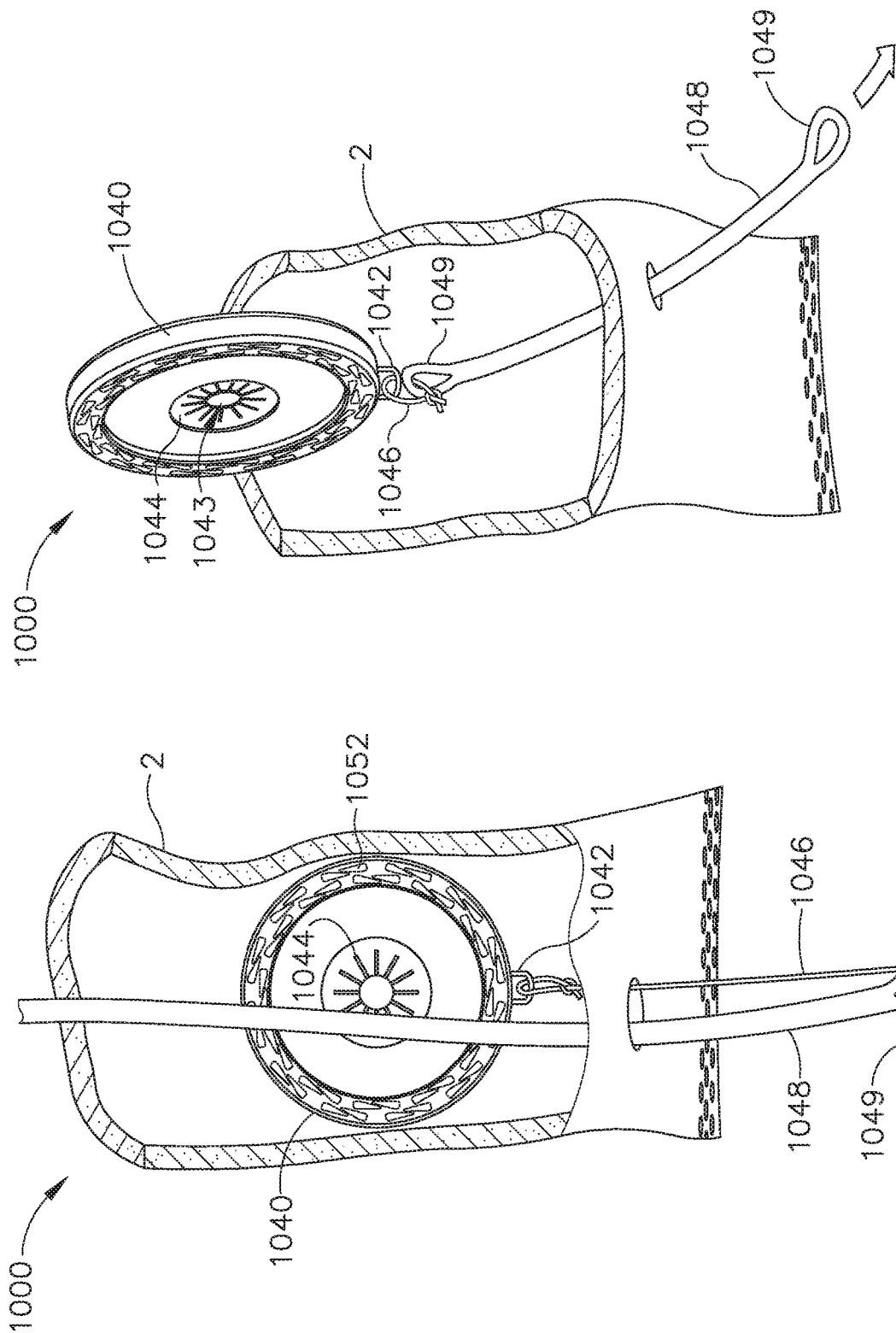

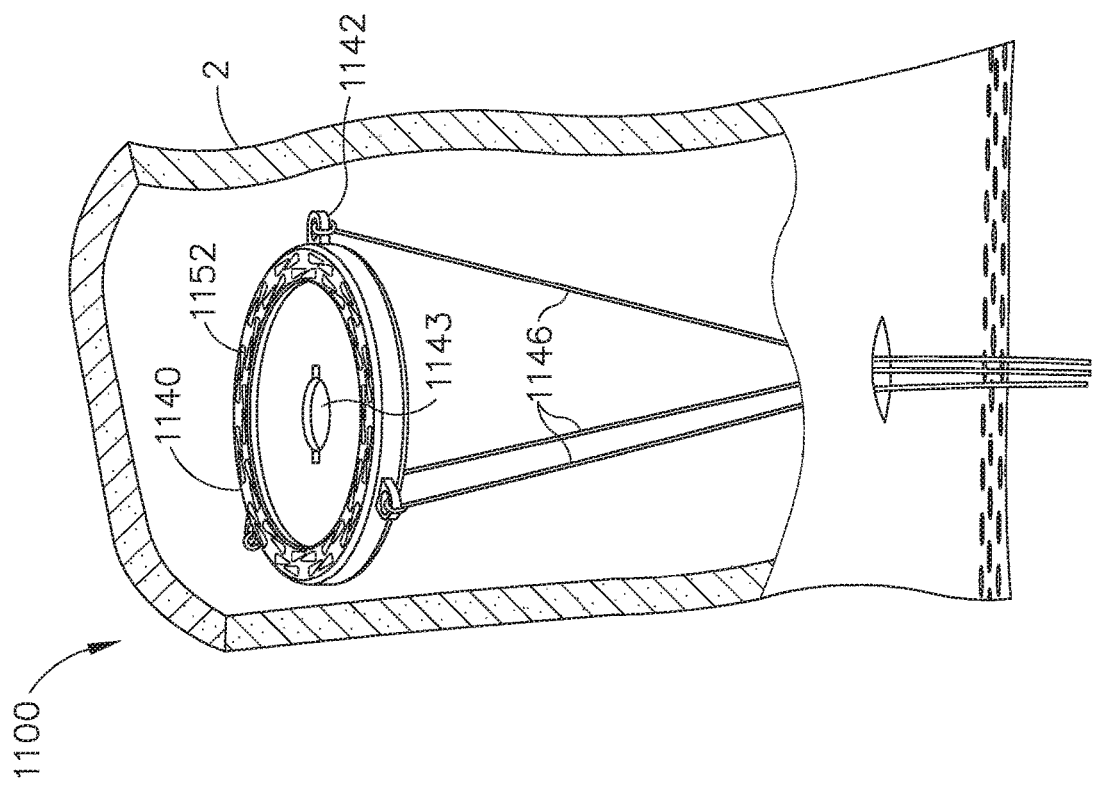
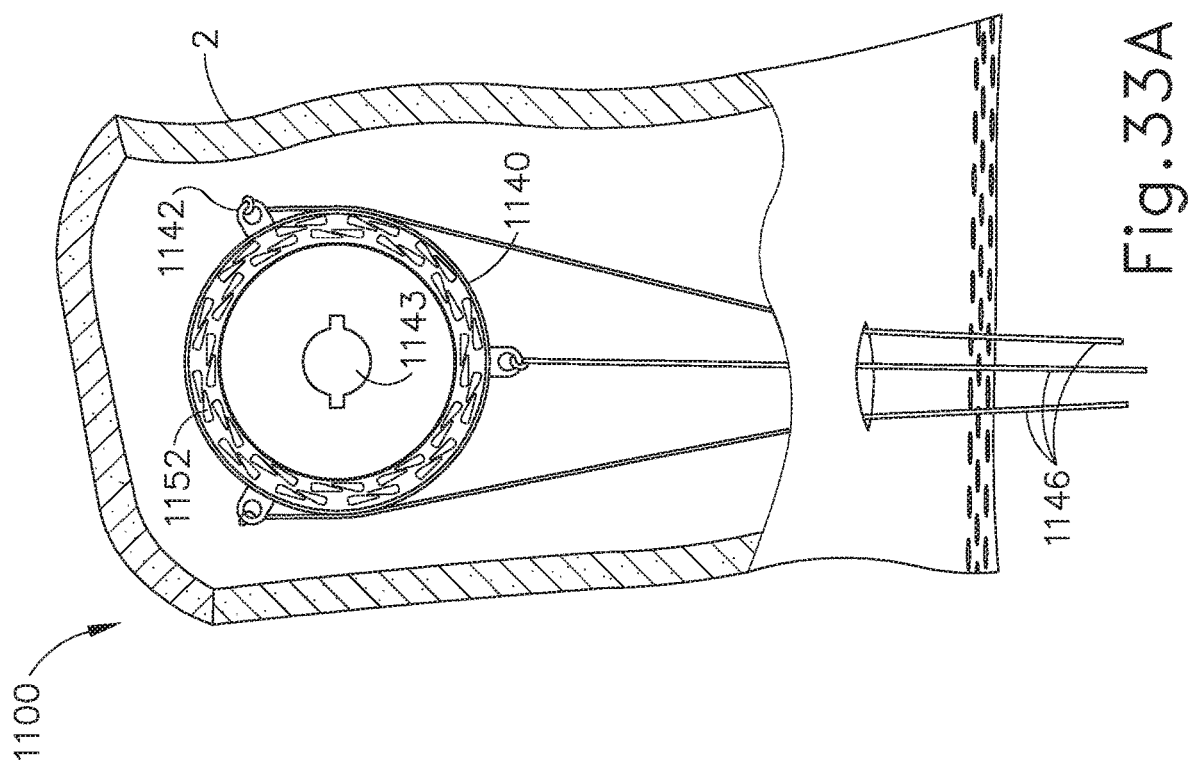

CIRCULAR ANVIL INTRODUCTION SYSTEM WITH ALIGNMENT FEATURE

This application is a continuation of U.S. patent application Ser. No. 13/693,455, filed Mar. 13, 2013, entitled "Circular Anvil Introduction System with Alignment Feature," issued as U.S. Pat. No. 9,724,100 on Aug. 8, 2017.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument." issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism." issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission." issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 8A depicts a cross sectional view of an exemplary anvil introduction assembly, suited for use with the stapler system if FIG. 7, showing an anvil sleeve removed from an anvil;

FIG. 8B depicts a cross sectional view of the anvil introduction assembly of FIG. 8A showing the anvil sleeve being inserted into the anvil;

FIG. 8C depicts a cross sectional view of the anvil introduction assembly of FIG. 8A showing the anvil sleeve inserted within the anvil:

FIG. 14 depicts an enlarged perspective view of another exemplary anvil;

FIG. 15A depicts a partial perspective view of the anvil of FIG. 14 positioned for coupling with a trocar;

FIG. 15B depicts a partial perspective view of the anvil and trocar of FIG. 15A showing the anvil being coupled to the trocar;

FIG. 15C depicts a partial perspective view of the anvil and trocar of FIG. 15A showing the anvil coupled to the trocar, with an anvil locking feature in an expanded position:

FIG. 22 depicts a partial perspective view of another exemplary trans-oral circular anvil assembly;

FIG. 23 depicts a cross sectional view of the anvil assembly of FIG. 22 being coupled to a trocar;

FIG. 24A depicts a cross sectional view of another exemplary trans-oral circular anvil assembly showing an anvil being coupled to a trocar;

FIG. 24B depicts a cross sectional view of the anvil assembly and trocar of FIG. 24A showing the trocar partially inserted in the anvil;

FIG. 25A depicts a partial perspective view of another exemplary trans-oral circular anvil assembly, disposed in a transected esophagus section;

FIG. 25B depicts a cross sectional view of the anvil assembly of FIG. 25A showing the anvil being coupled to a trocar approaching from another transected esophagus section, with an anvil alignment feature in a collapsed position;

FIG. 25C depicts a cross sectional view of the anvil assembly of FIG. 25A showing the anvil sliding onto the trocar with the anvil alignment feature straightening:

FIG. 25D depicts a cross sectional view of the anvil assembly of FIG. 25A showing the anvil coupled to the trocar with the anvil alignment feature in a straightened position;

FIG. 26 depicts a cross sectional view of the anvil assembly of FIG. 25A showing the anvil alignment feature in the collapsed position;

FIG. 27 depicts a cross sectional view of the anvil alignment feature of FIG. 25A, taken along line 27-27 of FIG. 26;

FIG. 28 depicts a partial perspective view of another exemplary trans-oral circular anvil being pulled through an esophagus section by an instrument that is inserted trans-orally:

FIG. 29 depicts a partial perspective view the anvil of FIG. 28 being pulled through an esophagus section by an instrument that is inserted from the bottom of the esophagus section;

FIG. 33A depicts a partial perspective view of another exemplary trans-oral circular anvil being pulled through an esophagus section, with the anvil oriented in a vertical position;

FIG. 33B depicts partial perspective view the anvil of FIG. 33A, with the anvil oriented in a horizontal position;

Figure 6:
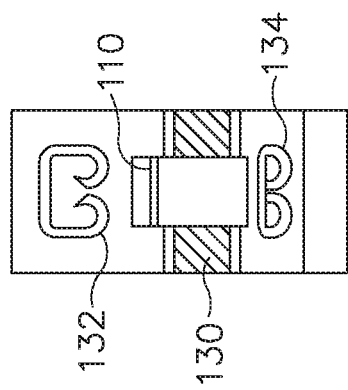
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
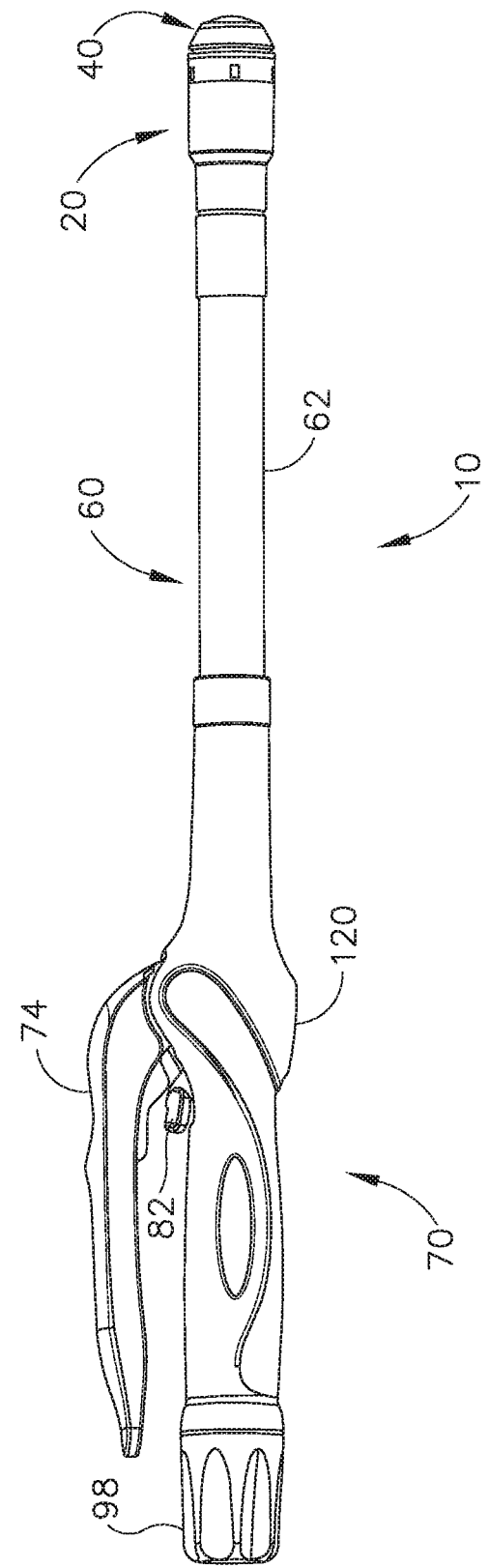
FIG. 1 depicts a side elevation view of an exemplary circular stapling surgical instrument.
Figure 2A:
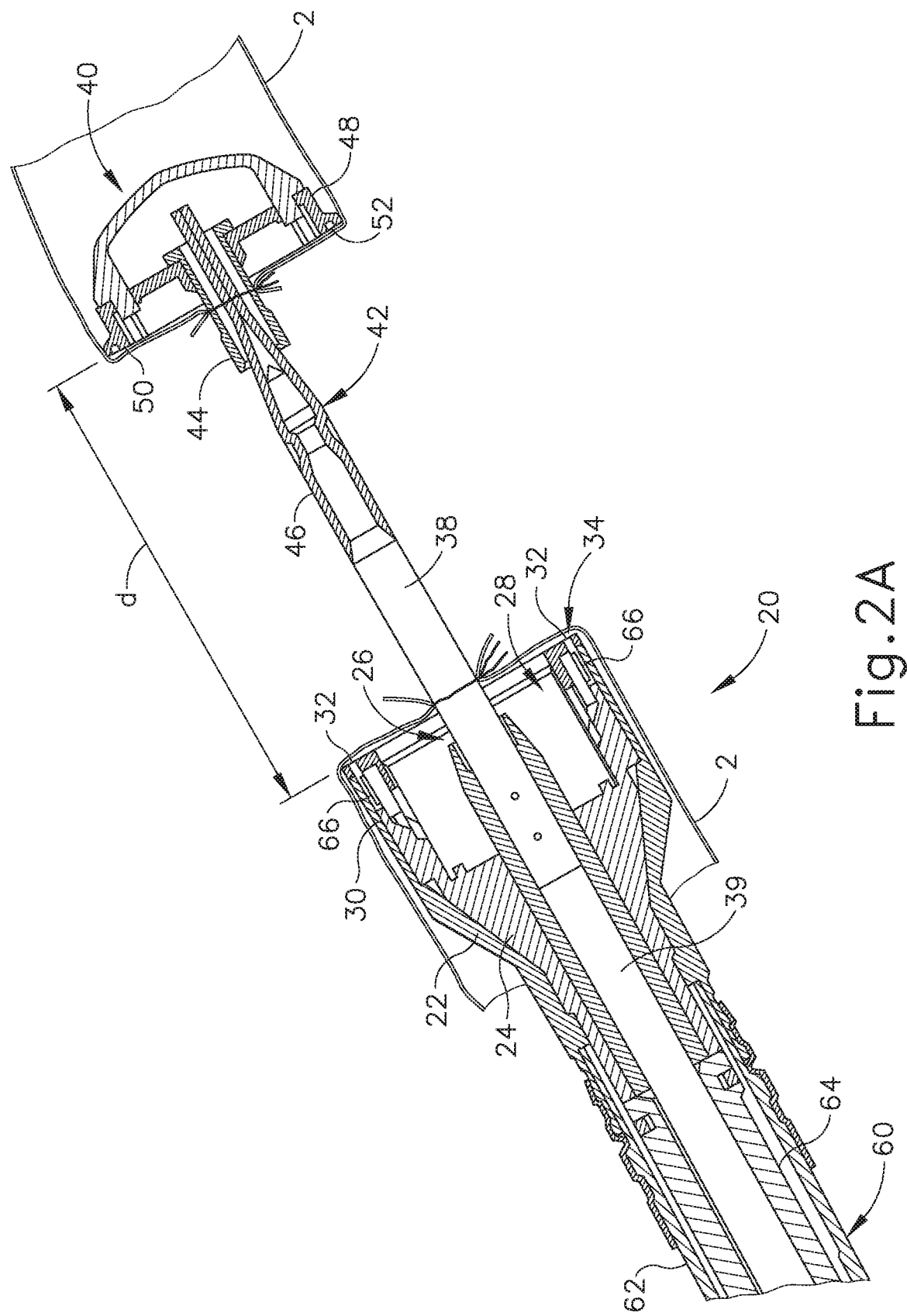
FIG. 2A depicts an enlarged longitudinal cross-section view of an exemplary stapling head assembly of the instrument of FIG. 1 showing an exemplary anvil in an open position.
Figure 2B:
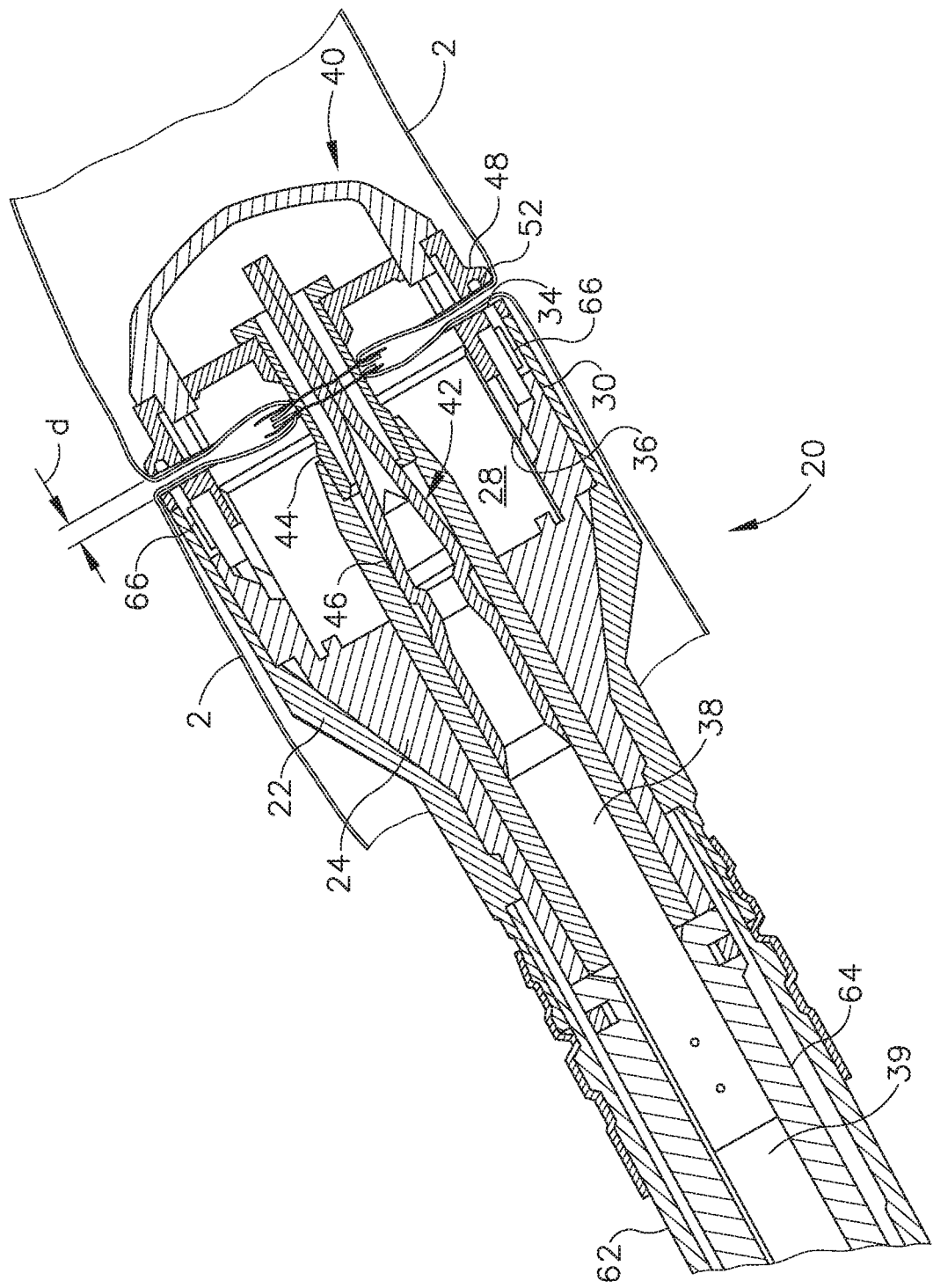
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
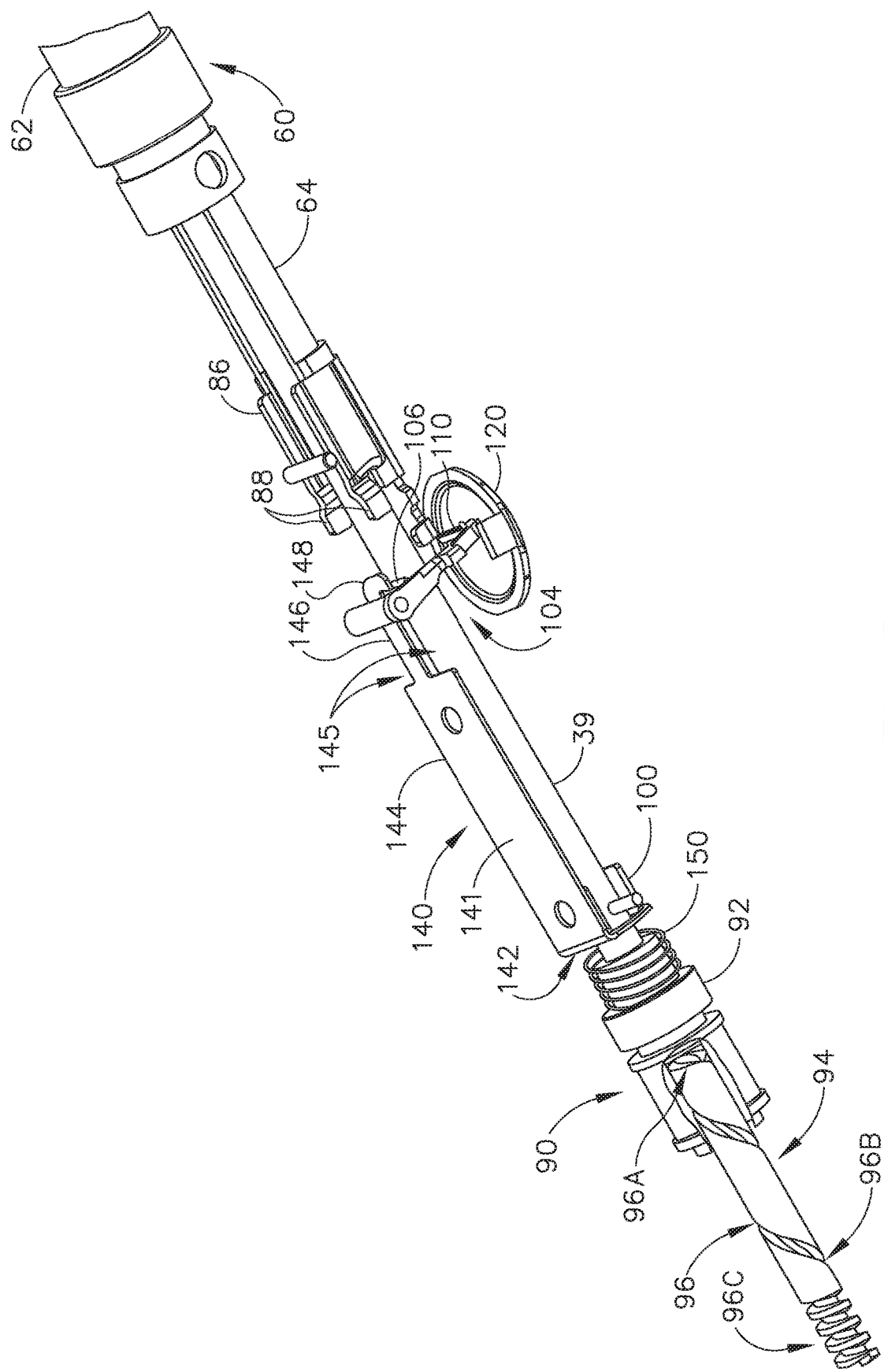
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
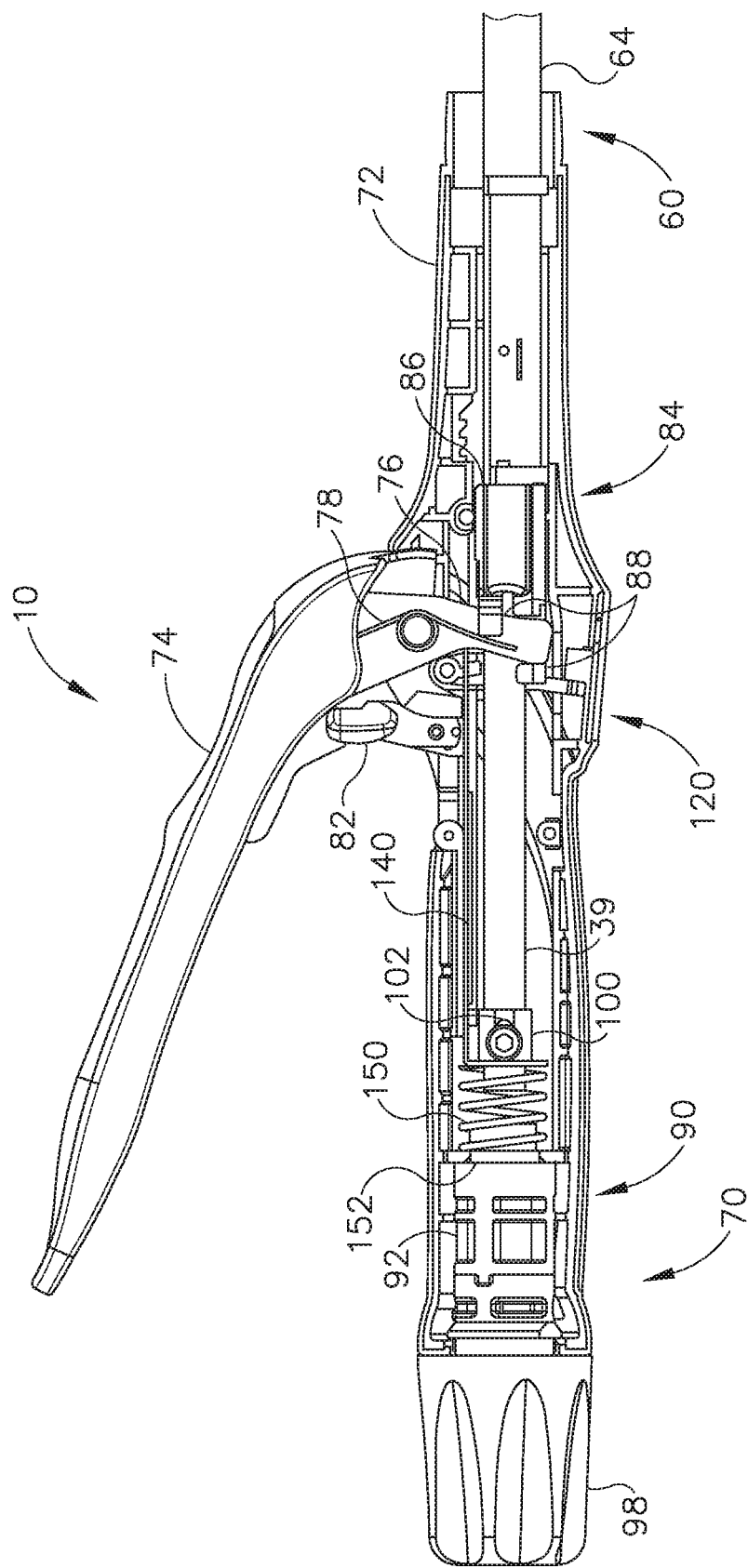
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
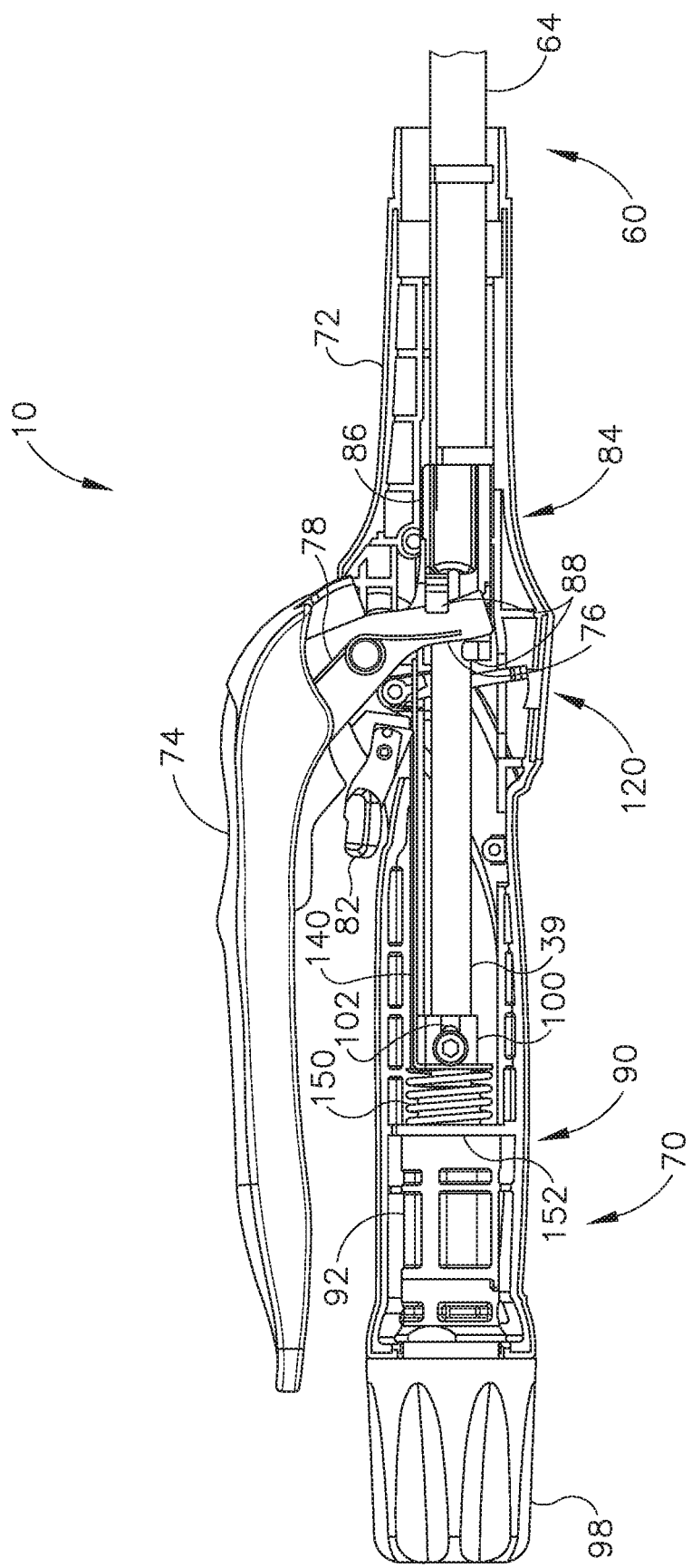
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B. 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Trans-Oral Circular Anvil Systems

Figure 7:
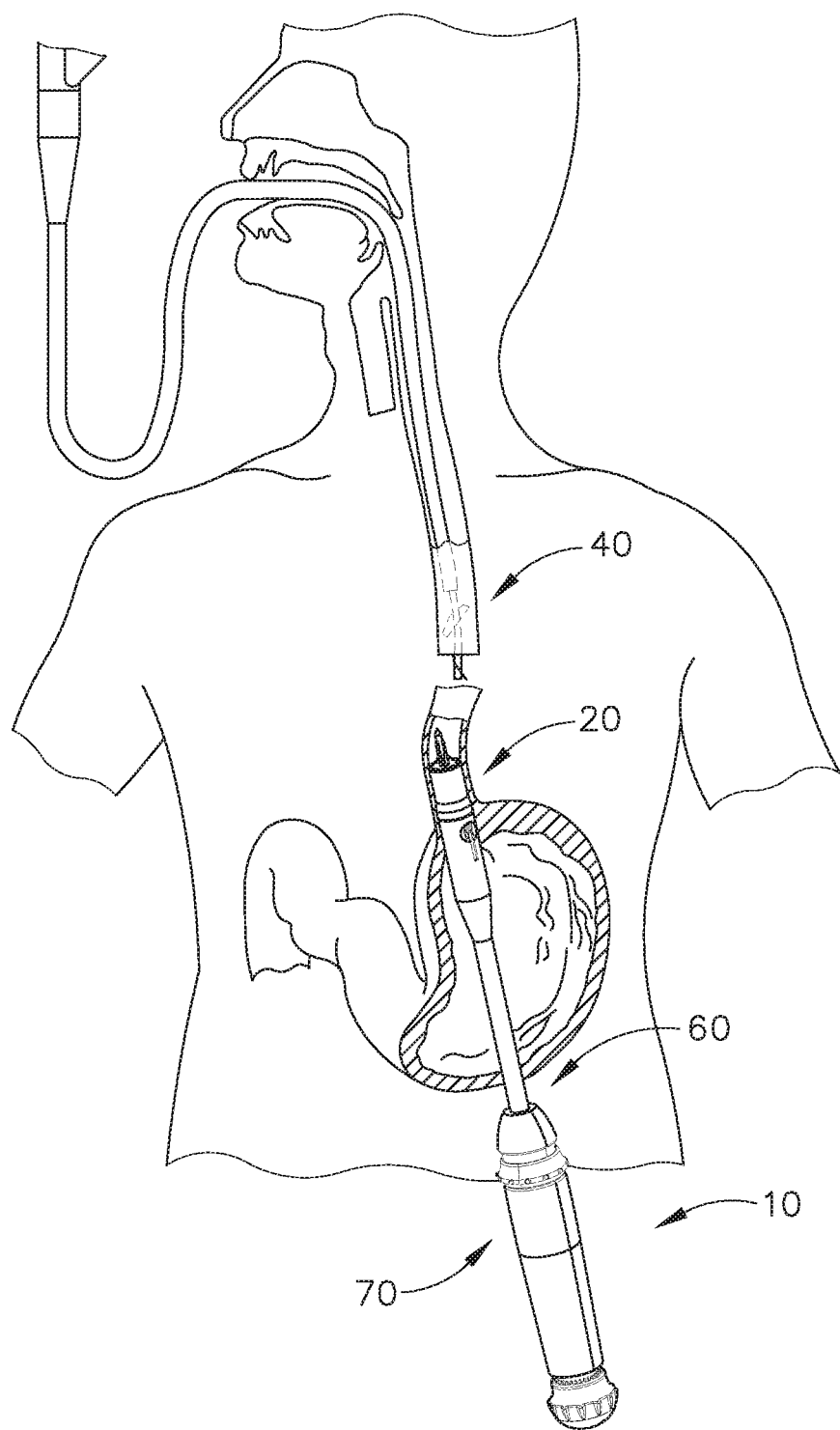
FIG. 7 depicts a schematic view of an exemplary circular stapler system being used in an esophagectomy procedure.

As described above, anvil (40) may be provided as a separate component such that anvil (40) may be inserted and secured to a portion of tissue (2) prior to being coupled to stapling head assembly (20). For instance, it may be desirable to introduce anvil (40) trans-orally for procedures within a patient's gastro-intestinal tract (e.g., an esophagectomy). FIG. 7 depicts an initial stage of an anastomosis procedure to couple severed esophagus sections (2, 4) following an esophagectomy. Anvil (40) is inserted trans-orally through the esophagus and is positioned within a first severed section (2) of the esophagus. Instrument (10) is inserted through the stomach and positioned within a second severed section (4) of the esophagus. Anvil (40) is then coupled to trocar (38) of instrument (10) to staple and seal severed sections (2, 4) of the esophagus in an anastomosis. Anvil (40) may also be inserted within other bodily lumens or regions of the gastro-intestinal tract to perform an anastomosis as will be apparent to one with ordinary skill in the art in view of the teachings herein. After insertion, it may be desirable to provide a trans-oral circular anvil locking assembly to couple anvil (40) to trocar (38). It may also be desirable to align staple pockets (52) with staples (66) of stapling head assembly (20) with an anvil alignment assembly. Anvil (40) may be introduced through a naturally occurring bodily lumen (e.g. the esophagus) to couple anvil (40) to trocar (38) using an anvil introduction system. The examples below include several versions of anvil (40) that may be readily introduced to an anastomosis site trans-orally. Several versions of rotational anvil alignment features are also described below that may be readily introduced to align staple pockets (52) of anvil (40) with staples (66) of stapling head assembly (20). Other examples of such features will be apparent to one with ordinary skill in the art in view of the teachings herein. It should be understood that the teachings below may be readily incorporated into instrument (10) as described above.

A. Exemplary Anvil Locking Features

FIGS. 8A-9D show an exemplary anvil locking assembly (200). Anvil locking assembly (200) comprises an anvil (240), an anvil sleeve (242), and a trocar (238). Anvil (240) is similar to anvil (40) described above. Anvil (240) has a disc-shaped configuration comprising a proximal surface (250) and a distal surface (248), with an inner opening (243). Anvil (240) further comprises staple pockets (252) aligned around proximal surface (250). Staple pockets (250) may also be formed on distal surface (248).

Anvil sleeve (242) is sized to be inserted within inner opening (243) of anvil (240). Anvil sleeve (242) comprises tabs (244) and suture (246). Tabs (244) may be resiliently biased to extend outwardly from anvil sleeve (242) as shown in FIG. 8A. Anvil sleeve (242) is inserted into inner opening (243) of anvil (240) through proximal surface (250), as also shown in FIG. 8A. As anvil sleeve (242) is inserted into anvil (240), tabs (244) are pushed against inner opening (243) to slide through inner opening (243), as shown in FIG. 8B. Once tabs (244) of anvil sleeve (242) are inserted past anvil (240), tabs (244) flip to their original position and extend outwardly from sleeve (244), as shown in FIG. 8C. Tabs (244) rest against distal surface (248) of anvil (240) to prevent anvil (240) from sliding distally off of anvil sleeve (242). Suture (246) of anvil sleeve (242) is then used to pull anvil (240) and anvil sleeve (242) through a naturally occurring bodily lumen (e.g., esophagus, colon, or other portion of the GI tract) to a desired location (e.g., an anastomosis site).

Figure 9A:
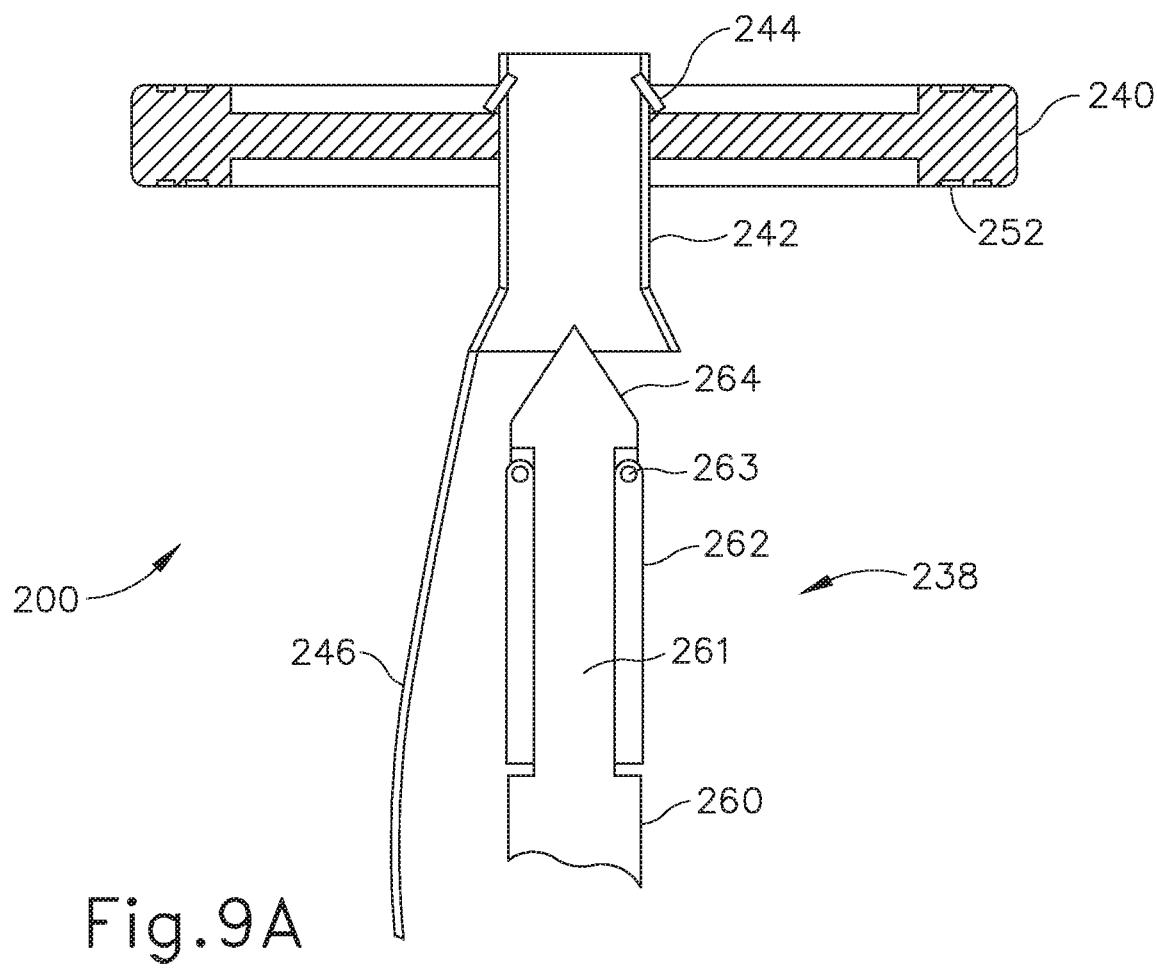
FIG. 9A depicts a cross sectional view of the anvil introduction assembly of FIG. 8A showing a trocar positioned for insertion into the anvil sleeve.
Figure 9B:
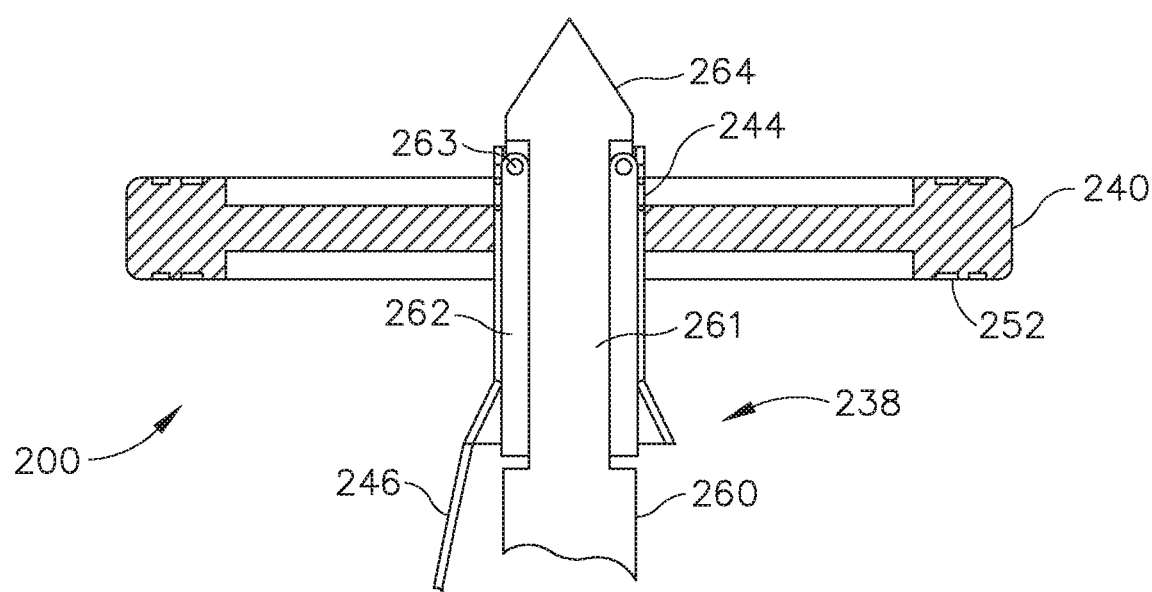
FIG. 9B depicts a cross sectional view of the anvil introduction assembly of FIG. 8A showing the anvil coupled to the trocar with an anvil locking feature in a collapsed position.
Figure 9C:
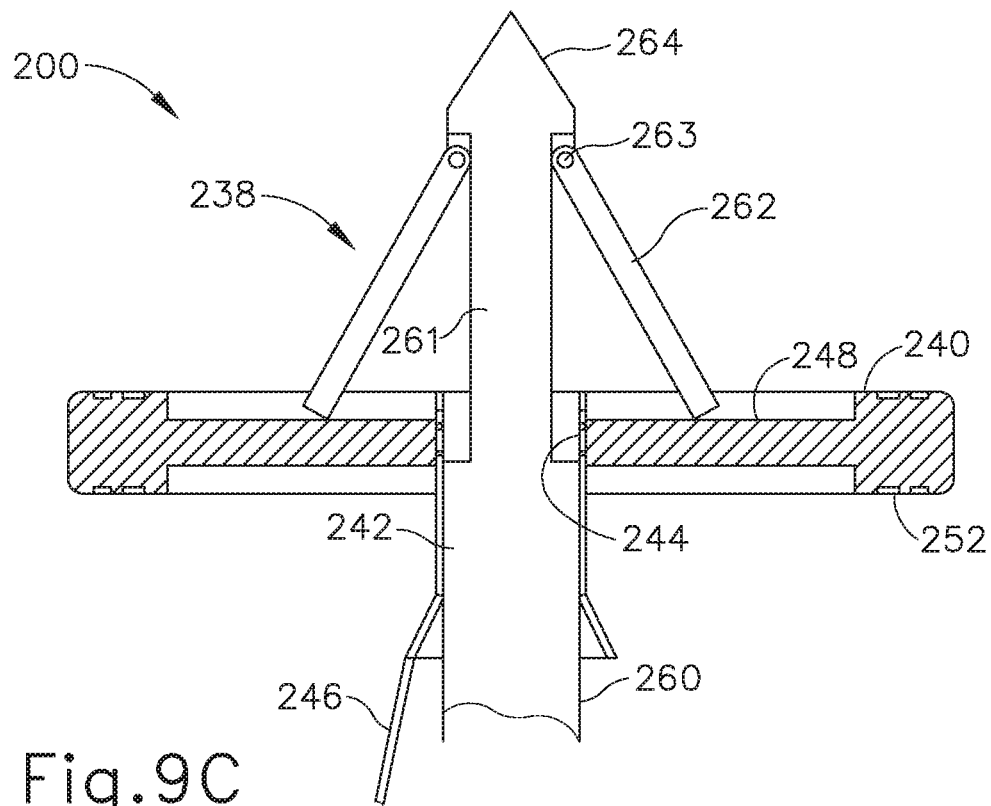
FIG. 9C depicts a cross sectional view of the anvil introduction assembly of FIG. 8A showing the anvil coupled to the trocar with the anvil locking feature in an expanded position.
Figure 9D:
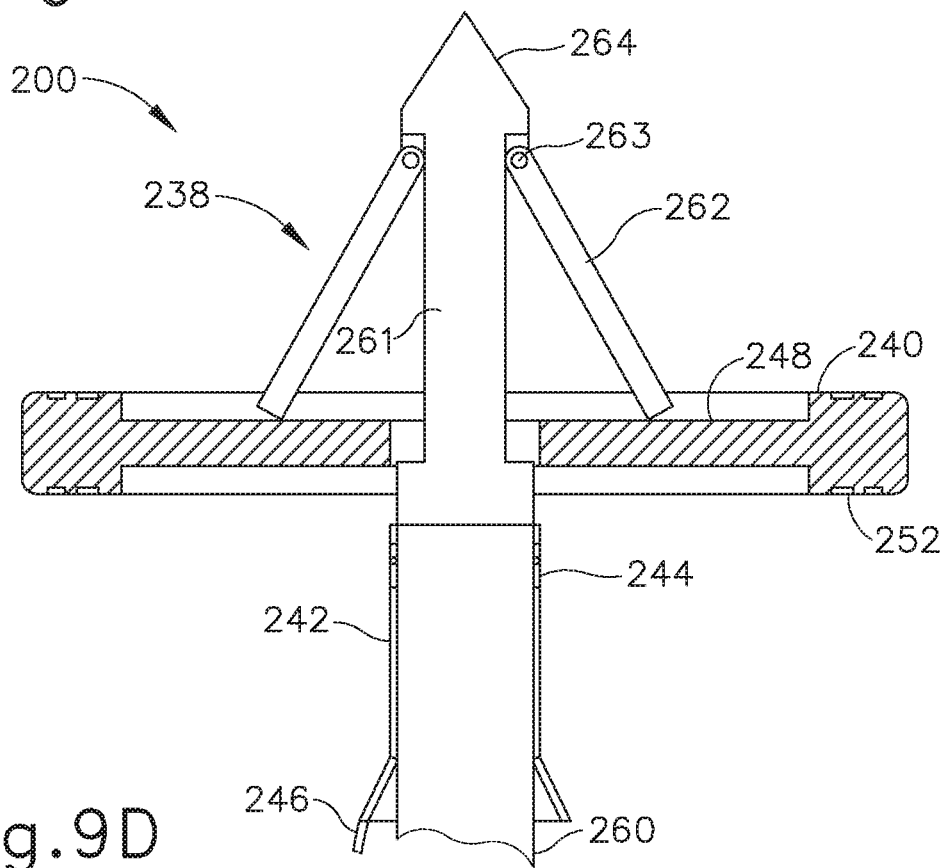
FIG. 9D depicts a cross sectional view of the anvil introduction assembly of FIG. 8A showing the anvil coupled to the trocar with the anvil locking feature in the expanded position and the anvil sleeve being removed.

Once anvil (240) is positioned at a desired location within the patient, trocar (238) is coupled to anvil (240), as shown in FIGS. 9A-9D. Trocar (238) comprises shaft (260), interior shaft (261), tip (264), and wings (262). Shaft (260) is sized to correspond to inner opening (243) of anvil (240). Tip (264) is positioned on the distal end of shaft (260). Interior shaft (261) is positioned along shaft (260) proximal to tip (264) and comprises a smaller diameter than shaft (260). Wings (262) are coupled to trocar (238) such that wings (262) are positioned along interior shaft (261) and are flush with shaft (260). Wings (262) pivot relative to trocar (238) via pins (263). Tip (264) of trocar (238) is inserted into inner opening (243) of anvil (240) through anvil sleeve (242). The taper of tip (264) and the flared configuration of the proximal end of anvil sleeve (242) assist in guiding trocar (238) into anvil sleeve (242). As trocar (238) moves distally through anvil (240), shaft (260) and wings (262) contact tabs (244) of anvil sleeve (242) to rotate tabs (244) flush with sleeve (242), as shown in FIG. 9B. When tabs (244) are rotated, suture (246) is pulled proximally to slide anvil sleeve (242) proximally through anvil (240). As sleeve (242) is pulled proximally, trocar (238) continues to be pushed distally through anvil (240). When wings (262) of trocar (238) are pushed past anvil (240), wings (262) pivot outwardly relative to shaft (261). Wings (262) may be resiliently biased to pivot outwardly to flared positions; or wings (262) may be actuated to pivot to such positions. Wings (262) then rest against distal surface (248) of anvil (240) to lock trocar (238) relative to anvil (240), as shown in FIG. 9C. Sleeve (242) continues to be pulled proximally along shaft (262) of trocar (238) to remove sleeve (242) from anvil (240), as shown in FIG. 9D. Alternatively, sleeve (242) may be torn apart to completely remove sleeve (242) from shaft (262) of trocar (238). Suitable methods for removing sleeve (242) will be apparent to one with ordinary skill in the art in view of the teachings herein.

Figure 10:
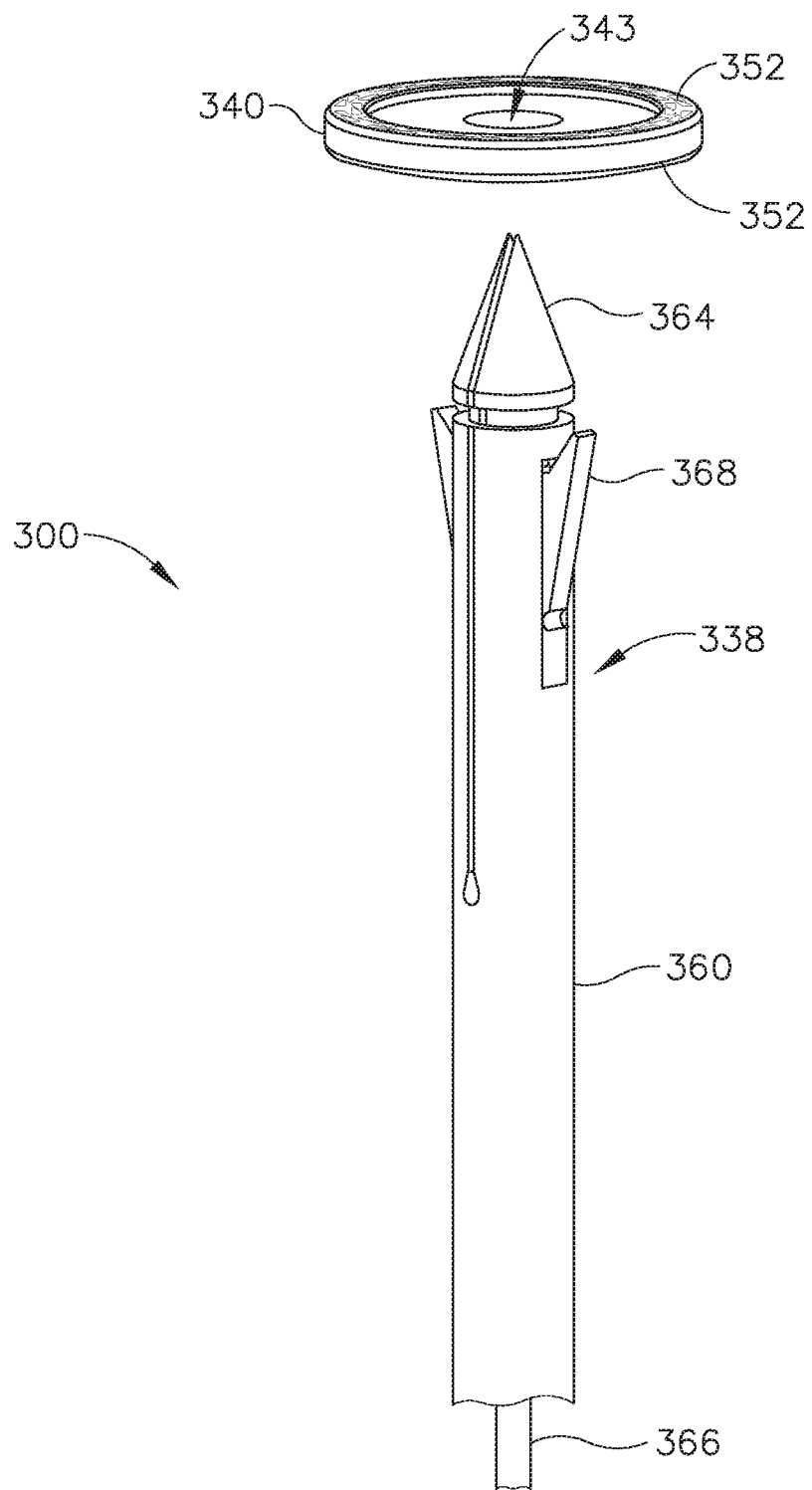
FIG. 10 depicts an enlarged partial perspective view of another exemplary trans-oral circular anvil removed from a trocar.
Figure 11A:
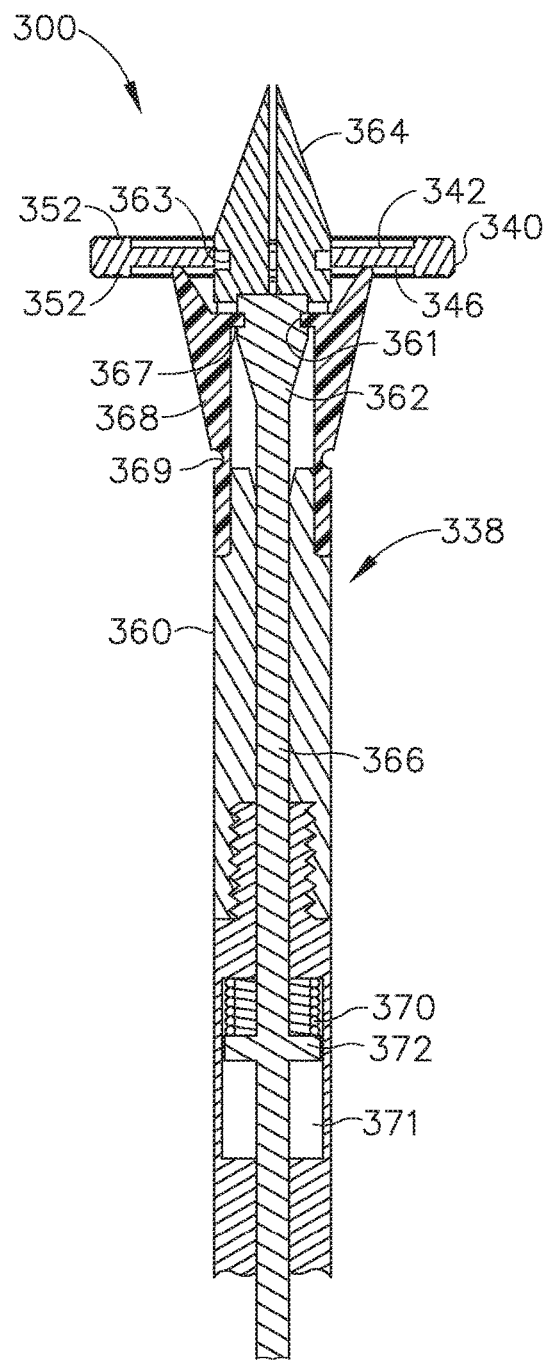
FIG. 11A depicts a cross sectional view of the anvil and trocar of FIG. 10 showing the anvil being positioned for coupling with the trocar, with an anvil locking feature in a collapsed position.
Figure 11B:
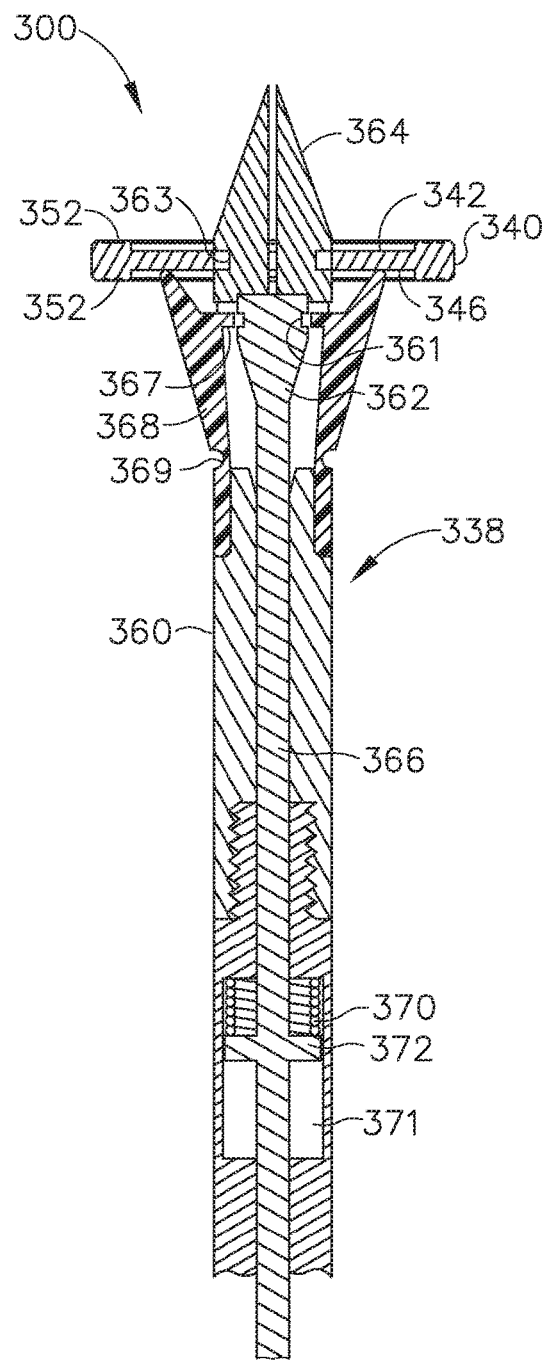
FIG. 11B depicts a cross sectional view of the anvil and trocar of FIG. 10 showing the anvil coupled to the trocar, with the anvil locking feature in a collapsed position.
Figure 11C:
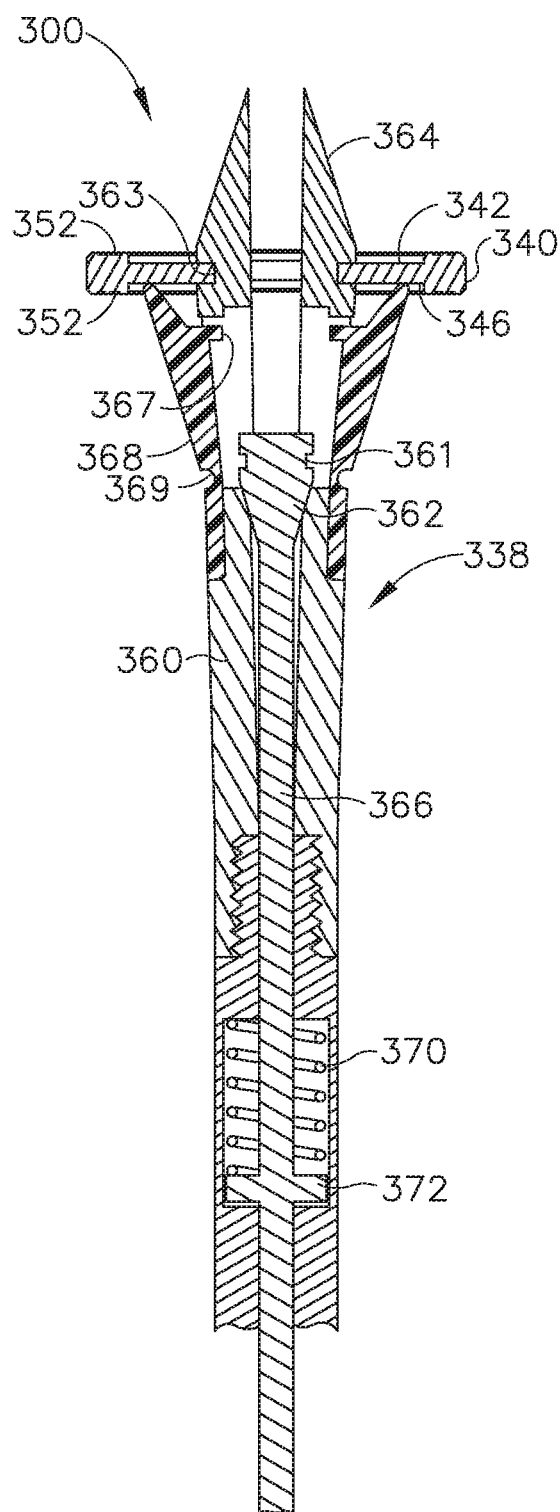
FIG. 11C depicts a cross sectional view of the anvil and trocar of FIG. 10 showing the anvil coupled to the trocar, with the anvil locking feature in an expanded position.

Another exemplary anvil locking assembly (300) is shown in FIGS. 10-11C. Anvil locking assembly (300) comprises an anvil (340) and a trocar (338). Anvil (340) is similar to anvil (240) described above. Anvil (340) comprises an inner opening (343) and staple pockets (352) aligned around a surface of anvil (340). Anvil (340) may also be dual-sided such that staple pockets (252) may be formed on both surfaces of disc-shaped anvil (340). Trocar (338) comprises an expanding tip (364), shaft (360), inner member (366) and fins (368). Expanding tip (364) is configured to fit within inner opening (343) of anvil (340) and comprises recesses (363). Recesses (363) align and correspond to the wall of inner opening (343) of anvil (340). Expanding tip (364) is positioned distal to shaft (360). Inner member (366) is positioned within shaft (360) such that inner member (366) translates relative to shaft (360). Inner member (366) comprises a camming portion (362) at the distal end of inner member (366). Camming portion (362) comprises recesses (361). Inner member (366) further comprises a flange (372) to retain resilient member (370) within an interior recess (371) of shaft (360). Resilient member (370) is biased to push flange (372) and inner member (366) proximally within shaft (360). Fins (368) are coupled to shaft (360) such that fins (368) pivot relative to shaft (360) via living hinges (369). Fins (368) are resiliently biased inward toward shaft (360). Fins (368) comprise inwardly extending protrusions (367) that correspond to recesses (361) of camming portion (362).

As shown in FIGS. 11A-11C, trocar (338) is inserted into anvil (340) to lock anvil (340) relative to trocar (338). As shown in FIG. 11A, anvil (340) is being coupled to trocar (338). Before the wall of inner opening (343) of anvil (340) reach recesses (363) of expanding tip (364), fins (368) are in a collapsed position such that protrusions (367) of fins (368) are engaged with recesses (361) of camming portion (362). Protrusions engage with recesses (361) to longitudinally fix inner member (366) relative to shaft (360). With expanding tip (364) in a collapsed position, tip (364) is inserted further into inner opening (343) of anvil (340). As shown in FIG. 11B, tip (364) of trocar (338) is further inserted into anvil (340) to align the wall of inner opening (343) with recesses (363). As anvil (340) is aligned around trocar (338), anvil (340) contacts fins (368) to pivot fins (368) outward from shaft (360) via living hinges (369). When fins (368) rotate outwardly, protrusions (367) disengage recesses (361) of inner member (366). This unlocks inner member (366) from fins (368) to allow inner member (366) to longitudinally translate relative to shaft (360). As shown in FIG. 11C, resilient member (370) pushes flange (372) of inner member (366) proximally relative to shaft (360) in response to inner member (366) being unlocked from fins (368). As inner member (366) translates proximally, camming portion (362) slides proximally to push expanding tip (364) outwardly to an expanded position. Recesses (363) of expanding tip (364) then engage the wall of inner opening (343) of anvil (340) to lock anvil (340) relative to trocar (338). Actuator (39) is then used to adjust the gap distance d between anvil (340) and trocar (338). Trigger (74) is actuated to drive stapling head assembly (20) to perform an anastomosis between the severed sections of the esophagus.

B. Exemplary Anvil Locking and Alignment Features

In addition to securing an anvil (40) to a trocar (38), anvil (40) is rotationally aligned with trocar (38) such that staple pockets (53) of anvil (40) are aligned with staples (66). Various examples of such rotational alignment features will be described in greater detail below, while other examples will be apparent to one with ordinary skill in the art in view of the teachings herein.

1. Exemplary Pivoting Tabs

Figures 12A, 12B:
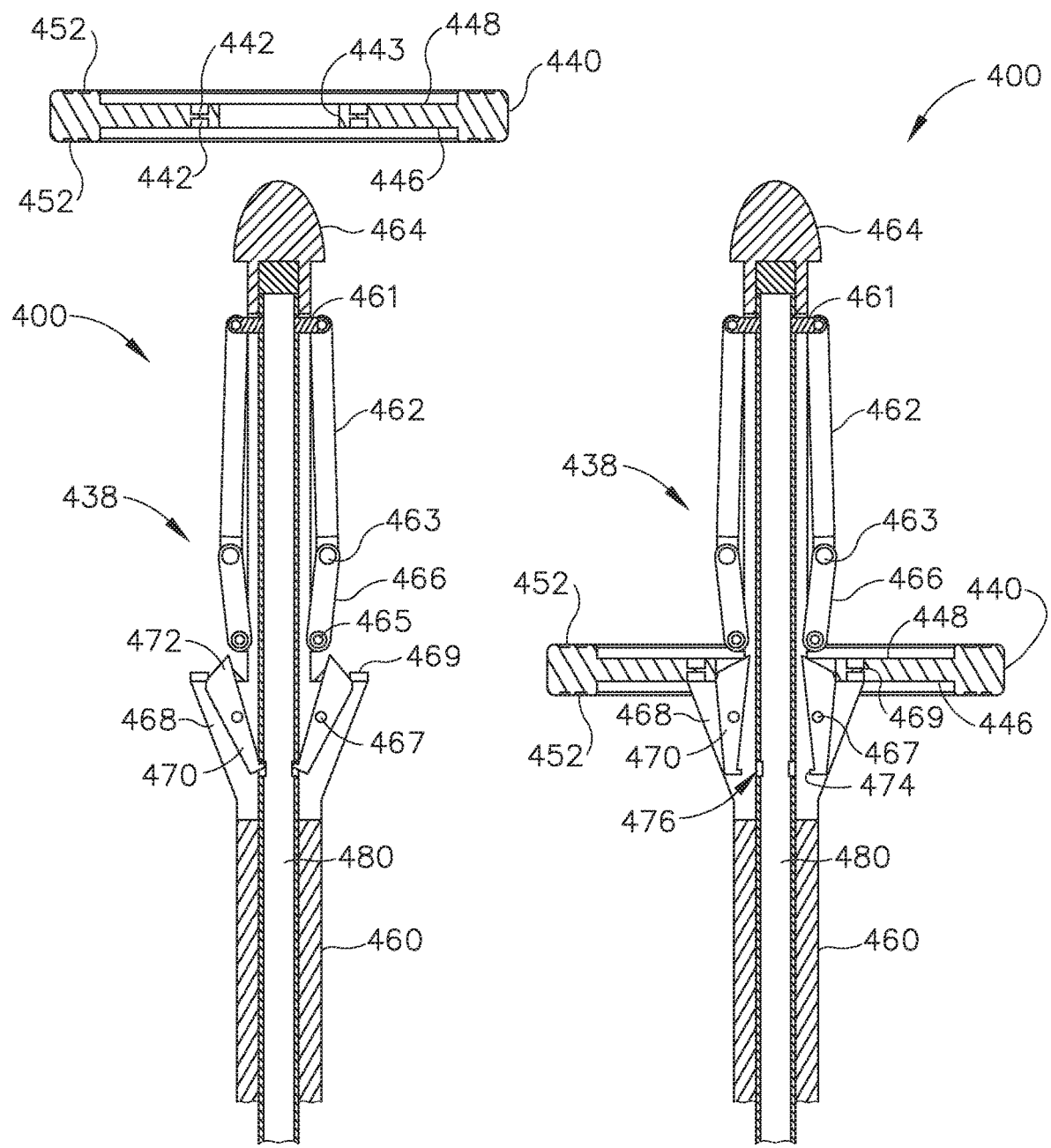
FIG. 12A depicts a cross sectional view of another exemplary trans-oral circular anvil removed from a trocar.
FIG. 12B depicts a cross sectional view of the anvil and trocar of FIG. 12A showing the anvil coupled to the trocar, with an anvil locking feature in a collapsed position.
Figure 12C:
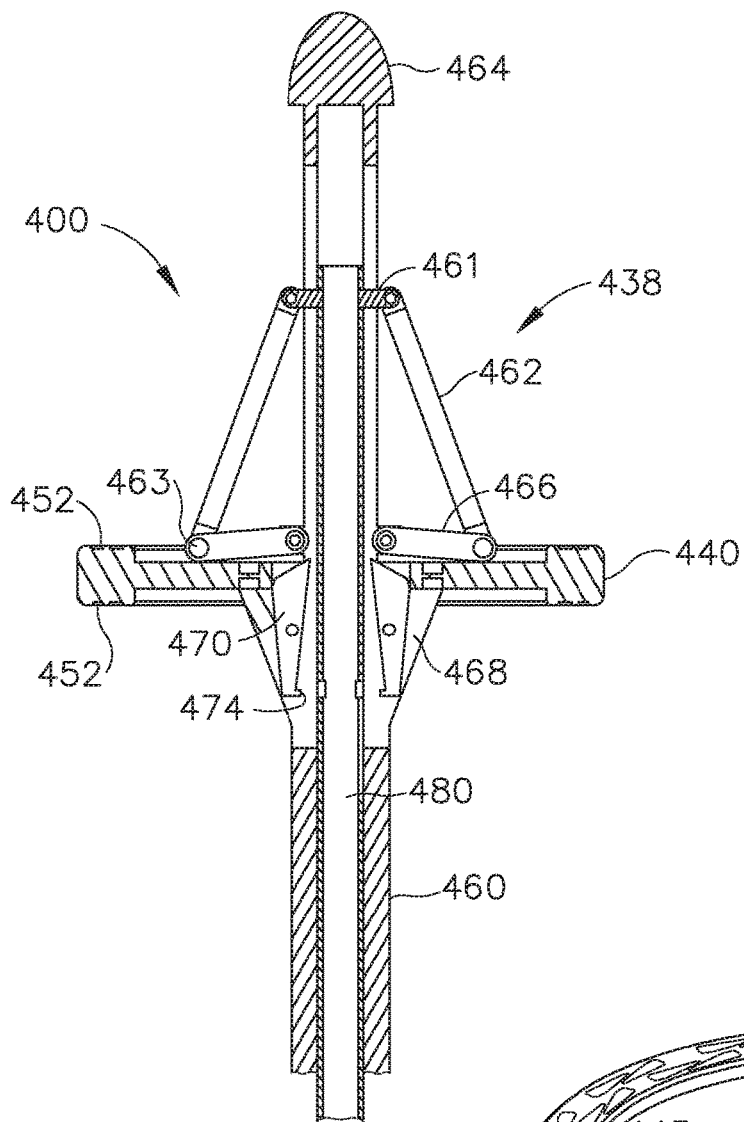
FIG. 12C depicts a cross sectional view of the anvil and trocar of FIG. 12A showing the anvil coupled to the trocar, with the anvil locking feature in an expanded position.
Figure 13:
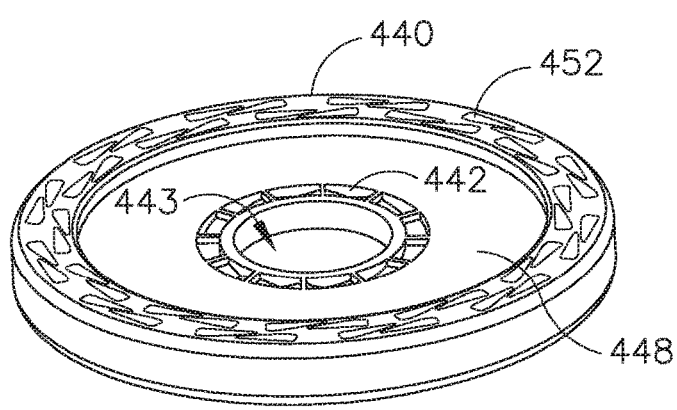
FIG. 13 depicts an enlarged perspective view of the anvil of FIG. 12A.
Figure 16:
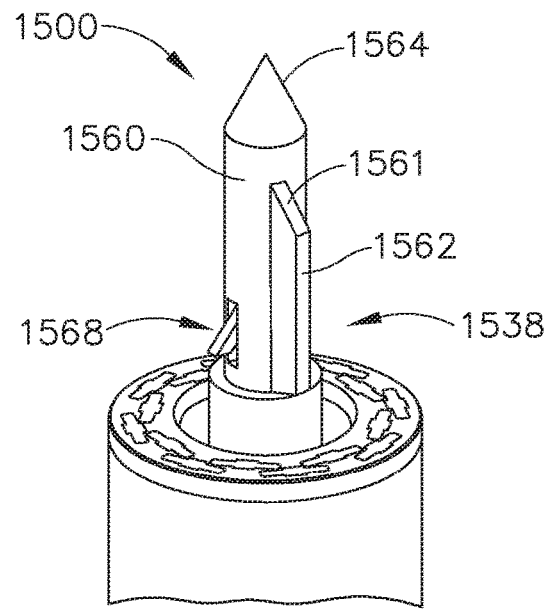
FIG. 16 depicts a partial perspective view of another exemplary trocar.

FIGS. 12A-13 show an exemplary anvil alignment assembly (400). Anvil alignment assembly comprises anvil (440) and trocar (438). Anvil (440) is similar to anvil (340), except that anvil (440) further comprises alignment features (442). As shown in FIG. 13, a plurality of alignment features (442) are aligned around inner opening (443) of anvil (440). Alignment features (442) comprise recesses extending inwardly around anvil (440). Trocar (438) comprises a tip (464), a shaft (460), inner member (480), fins (468), and expanding members (462, 466). Tip (464) is positioned on the distal end of shaft (460). Shaft (460) comprises fins (468) that extend outwardly from shaft (460). Fins (468) comprise engagement features (469) and tabs (470). Engagement features (469) comprise protrusions extending distally from fins (468) and are configured to complement and engage alignment features (442) of anvil (440). Tabs (470) pivot relative to fins (468) via pins (467). Tabs (470) comprise camming surfaces (472) and protrusions (474). Protrusions (474) fit within openings (476) of inner member (480), which is translatable relative to shaft (460). First expanding member (462) is coupled to a protrusion (461) of inner member (469). First expanding member (462) pivots outwardly relative to shaft (460). Second expanding member (466) is coupled to first expanding member (462) via pins (463). Second expanding member (466) is coupled to shaft (460) proximal to first expanding member (462) via pins (465). Second expanding member (466) also pivots outwardly relative to shaft (460). Although two sets of expanding members (462, 466) are shown, any other suitable number may be used.

As shown in FIG. 12A, trocar (438) is coupled to anvil (440) when anvil alignment assembly (400) is in a collapsed configuration. In this configuration, expanding members (462, 466) rest against shaft (460). Tabs (470) are rotated outwardly such that protrusions (474) are engaged with openings (476) of inner member (480). This fixes inner member (480) relative to shaft (460). Tip (464) of trocar (438) is then inserted into inner opening (443) of anvil (440), as shown in FIG. 12B. As trocar (438) is inserted into anvil (440), engagement features (469) of fins (468) are inserted into alignment features (442) of anvil (440). This ensures that anvil (440) is rotated to a position where staple pockets (452) are aligned with staples (66) of stapling head assembly (20). Camming surfaces (472) of tabs (470) engage the wall of inner opening (443) to rotate tabs (470) inward as trocar (438) is inserted into anvil (400). When tabs (470) rotate inward, protrusions (474) unlock from openings (476) of inner member (480). This allows inner member (480) to translate relative to shaft (460). As shown in FIG. 12C, inner member (480) is translated proximally relative to shaft (460) to expand anvil alignment assembly (400) to an expanded configuration. By way of example only, inner member (480) may be translated by a feature similar to resilient member (370) within a recess (371) of shaft (460) as described above. Other suitable ways in which inner member (480) may be translated will be apparent to one with ordinary skill in the art in view of the teachings herein. When inner member (480) translates proximally, protrusion (461) of inner member (480) also translates proximally. Because second expanding member (466) is fixed to shaft (460), the translation of inner member (480) causes a proximal end of first expanding member (462) to pivot outward from shaft (460) and a distal end of second expanding member (466) to pivot outward from shaft (460). Second expanding member (466) contacts anvil (440) to hold anvil (400) in place relative to trocar (438) between second expanding member (466) and fins (468). Actuator (39) is then used to adjust the gap distance d between anvil (340) and trocar (338). Trigger (74) is actuated to drive stapling head assembly (20) to perform an anastomosis between the severed sections of the esophagus.

2. Exemplary Ribbed Trocar

Another exemplary anvil alignment assembly (500) is shown in FIGS. 14-15C. Anvil alignment assembly (500) comprises anvil (540) and trocar (538). Anvil (540) is similar to anvil (340), except that anvil (540) further comprises alignment features (542). Alignment features (542) each comprise an angled surface (541). As shown in FIG. 14, a plurality of alignment features (542) are circumferentially spaced about the wall of inner opening (543) of anvil (540). Trocar (538) comprises a shaft (560), tip (564), ribs (562), and tabs (568). Shaft (560) extends from stapling head assembly (20). The diameter of shaft (560) gradually decreases as shaft (560) extends from stapling head assembly (20). Tip (564) is positioned on the distal end of shaft (560). At least one rib (562) extends along shaft (560). A suitable number of ribs (562) will be apparent to one with ordinary skill in view of the teachings herein. For instance, the number of ribs (562) may correspond with the number of alignment features (542). Tabs (568) extend and pivot relative to shaft (560).

As shown in FIGS. 15A-15C, trocar (538) is inserted into anvil (540). As trocar (538) is inserted, ribs (562) of shaft (560) engage alignment features (542) of anvil (540). Angled surfaces (541) of alignment features (542) urge anvil (540) to rotate into position to align with ribs (562). This also aligns staple pockets (552) of anvil (540) with staples (66) of stapling head assembly (20). Trocar (538) continues to be inserted through anvil (540). Tabs (568) of trocar (538) may be resiliently biased to an outward position. As anvil (540) travels over tabs (568), anvil (540) causes tabs (568) to pivot inwardly. Once anvil (540) passes tabs (568), tabs (568) then pivot back outwardly to engage the top surface of anvil (540), as shown in FIG. 15C. This holds anvil (540) in place relative to trocar (538). Actuator (39) is then used to adjust the gap distance d between anvil (540) and trocar (538). Trigger (74) is actuated to drive stapling head assembly (20) to perform an anastomosis between the severed sections of the esophagus.

Figure 17:
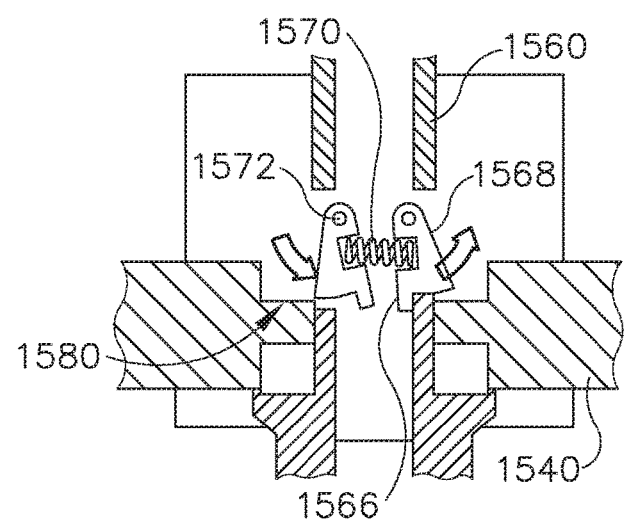
FIG. 17 depicts a cross sectional view of the trocar of FIG. 16.
Figure 18:
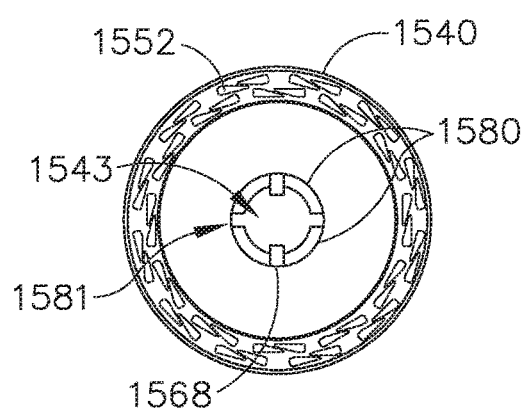
FIG. 18 depicts a top plan view of another exemplary anvil for coupling with the trocar of FIG. 16.
Figure 19:
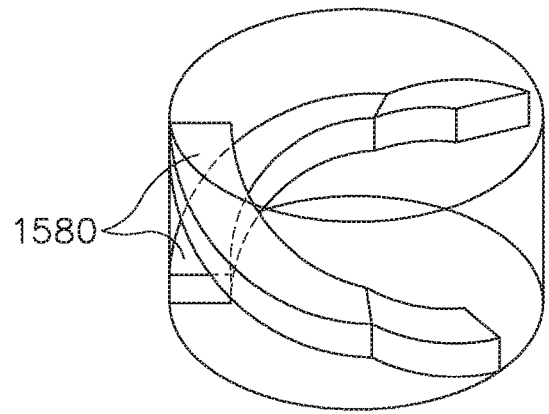
FIG. 19 depicts an enlarged partial perspective view of exemplary threading of the anvil of FIG. 18.

Another exemplary anvil alignment assembly (1500) is shown in FIGS. 16-19. Anvil alignment assembly (1500) comprises anvil (1540) and trocar (1538). Anvil (1540) is similar to anvil (540), except that anvil (1540) comprises a pair of alignment features (1580). As shown in FIGS. 18-19, the pair alignment features (1580) extend from the wall of inner opening (1543) of anvil (1540) and comprise a ramped configuration in the form of a coarse half-thread. The two alignment features (1580) extend around only a portion of the inner wall of opening (1543) to form recesses (1581) between alignment features (1580). The helical, ramped configuration of alignment features (1580) allow anvil (1540) to rotate into alignment. The ramped configuration of alignment features (1580) allow for a dual-sided anvil (1540) such that anvil (1540) is rotated by alignment features (1580) when trocar (1538) is inserted into either side of anvil (1540). Trocar (438) comprises a shaft (1560), tip (1564), a pair of ribs (1562), and tabs (1568). Shaft (1560) extends from stapling head assembly (20). Tip (1564) is positioned on the distal end of shaft (1560). Ribs (1562) extend along shaft (1560) to correspond to recesses (1581)

of anvil (1540). Ribs (1562) comprise angled surfaces (1561) to engage alignment features (1580) of anvil (1540) to guide anvil (1540) into rotational alignment. Tabs (1568) extend and pivot relative to shaft (1560). As shown in FIG. 17, tabs (1568) are resiliently biased outwardly by resilient member (1566). Tabs (1568) are angled to allow anvil (1540) to slide over and push tabs (1568) inwardly.

In an exemplary use, trocar (1538) is inserted into anvil (1540). As trocar (1538) is inserted, ribs (1562) of shaft (1560) engage alignment features (1580) of anvil (1540). The ramped configuration of alignment features (1580) allow anvil (1540) to rotate into position until ribs (1562) insert into recesses (1581). This also aligns staple pockets (1552) of anvil (1540) with staples (66) of stapling head assembly (20). Trocar (1538) continues to be inserted through anvil (1540). As anvil (1540) travels over tabs (1568), anvil (1540) causes tabs (1568) to pivot inwardly against resilient member (1566). Once anvil (1540) passes tabs (1568), resilient member (1566) then biases tabs (1568) back outward to engage the top surface of anvil (1540). This holds anvil (1540) in place relative to trocar (1538). Actuator (39) is then used to adjust the gap distance d between anvil (1540) and trocar (1538). Trigger (74) is actuated to drive stapling head assembly (20) to perform an anastomosis between the severed sections of the esophagus.

3. Exemplary Recessed Trocar

Figures 20, 21A:
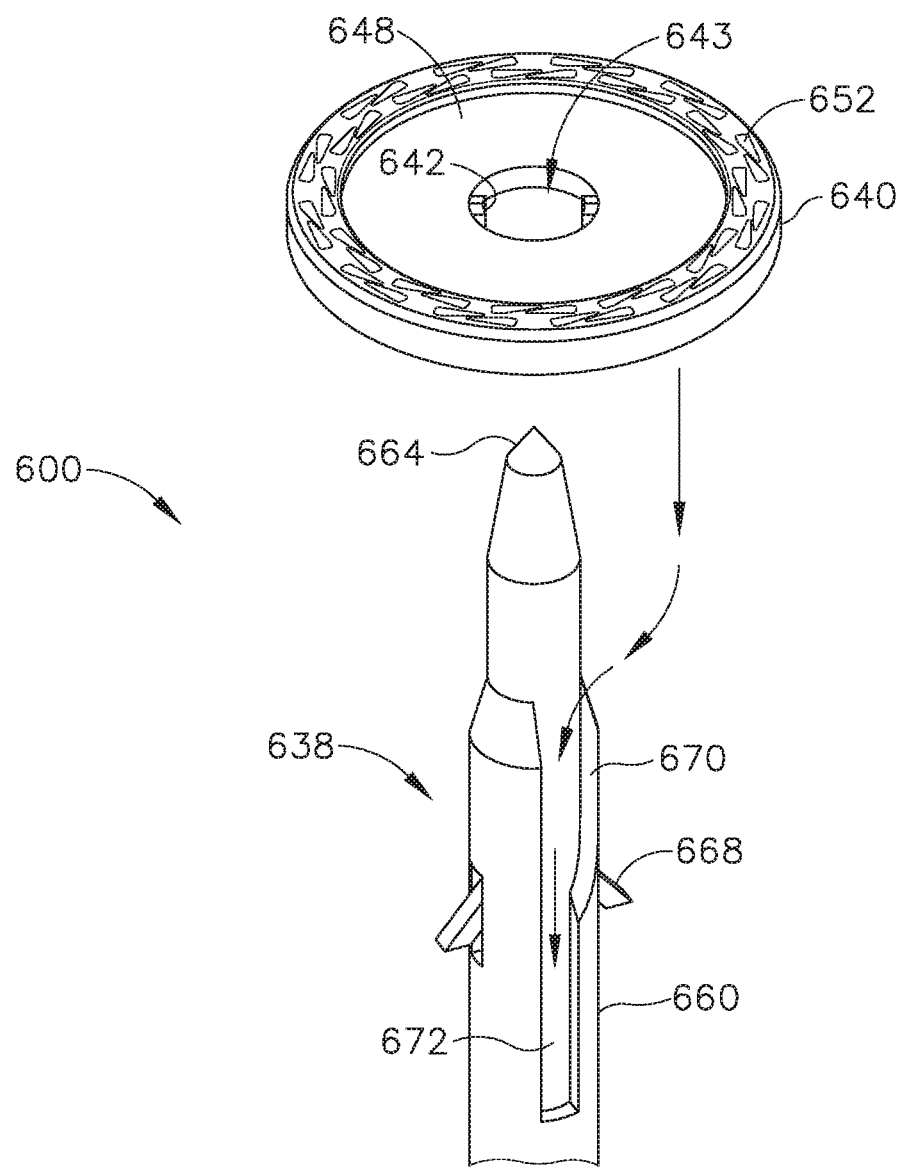
FIG. 20 depicts a cross sectional view of another exemplary anvil.
FIG. 21A depicts an enlarged partial perspective view of the anvil of FIG. 20 positioned for coupling with a trocar.
Figure 21B:
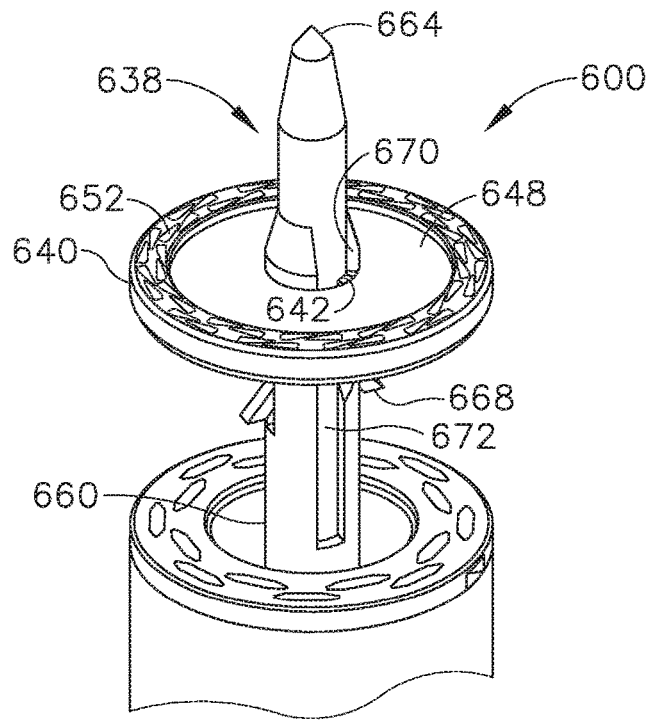
FIG. 21B depicts a partial perspective view of the anvil and trocar of FIG. 21A showing the anvil being coupled to the trocar.
Figure 21C:
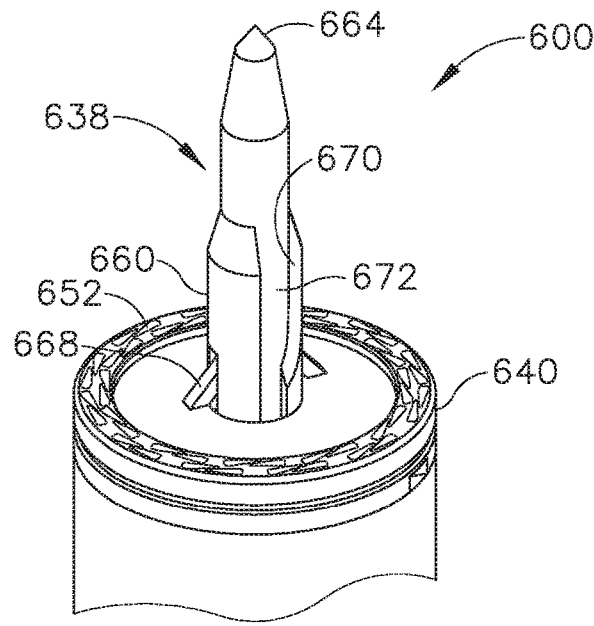
FIG. 21C depicts a partial perspective view of the anvil and trocar of FIG. 21A showing the anvil coupled to the trocar, with an anvil locking feature in an expanded position.

Alternatively, a trocar (638) shaft may comprise camming alignment recesses (672) instead of ribs (562), as shown in FIGS. 20-21C. Anvil alignment assembly (600) is similar to anvil alignment assembly (500), except that trocar (638) comprises recesses (672). Anvil (640) comprises alignment features (642) that extend from the wall of inner opening (643) to correspond to recesses (672) of trocar (638). Although two recesses (672) and two alignment features (642) are shown, any suitable number of recesses (672) may be used to correspond to any number of alignment features (642). Recesses (672) comprise camming surfaces (670) to guide alignment features (642) of anvil (640) into detents (672). This allows anvil (640) to rotate into position to align with recesses (672), which aligns staple pockets (652) of anvil (640) with staples (66) of stapling head assembly (20). Similar to anvil alignment assembly (500), tabs (668) of anvil alignment assembly (600) hold anvil (640) in place relative to trocar (638).

C. Exemplary Anvil Introduction and Locking Features

As shown in FIGS. 22-23, an anvil (740) is introduced through a naturally occurring bodily lumen (e.g. the esophagus) using an anvil introduction system (700). Anvil (740) is similar to anvil (40) described above. Anvil (740) further comprises a sleeve (750) extending from anvil shaft (744). Sleeve (750) comprises a flexible section (748), openings (742), and collar (749). Flexible section (748) allows sleeve (750) to deform to various angles and configurations, such as a 90 degree angle shown in FIG. 22. Openings (742) are located on opposing sides of the proximal end of sleeve (750). Collar (749) extends from sleeve (750) and is positioned proximal to openings (742). Collar (749) is formed from a rigid material. Anvil introduction system (700) further comprises suture (746) and tube (747). Suture (746) is wrapped through anvil (740) and sleeve (750) to form a loop. Suture (746) is then pulled through tube (747) to keep the ends of suture (746) together. Tube (747) and suture (746) is then used to pull anvil (740) through the esophagus (or some other region of the gastro-intestinal tract, etc.) to a desired stapling location.

Once in position, tube (747) and suture (746) is removed from anvil (740) and anvil (740) is coupled to trocar (738). Trocar (738) of this example comprises a shaft (760) extending from stapling head assembly (20). Shaft (760) comprises a tip (764) at the distal end of shaft (760) and resilient tabs (766) extending from shaft (760). Tip (764) of trocar (738) is inserted into sleeve (750) until tabs (766) align with openings (742) of sleeve (750). As trocar (738) is inserted into sleeve (750), collar (749) flexes tabs (764) inwardly to allow trocar (738) to slide into sleeve (750). Tabs (764) then flex outwardly through openings (742) to lock sleeve (750) relative to trocar (738). Flexible section (748) of sleeve (750) then bends to straighten sleeve (750) and align anvil (740) with stapling head assembly (20) as trocar (738) is pulled proximally to draw anvil (740) toward stapling head assembly (20).

Figures 24C, 24D:
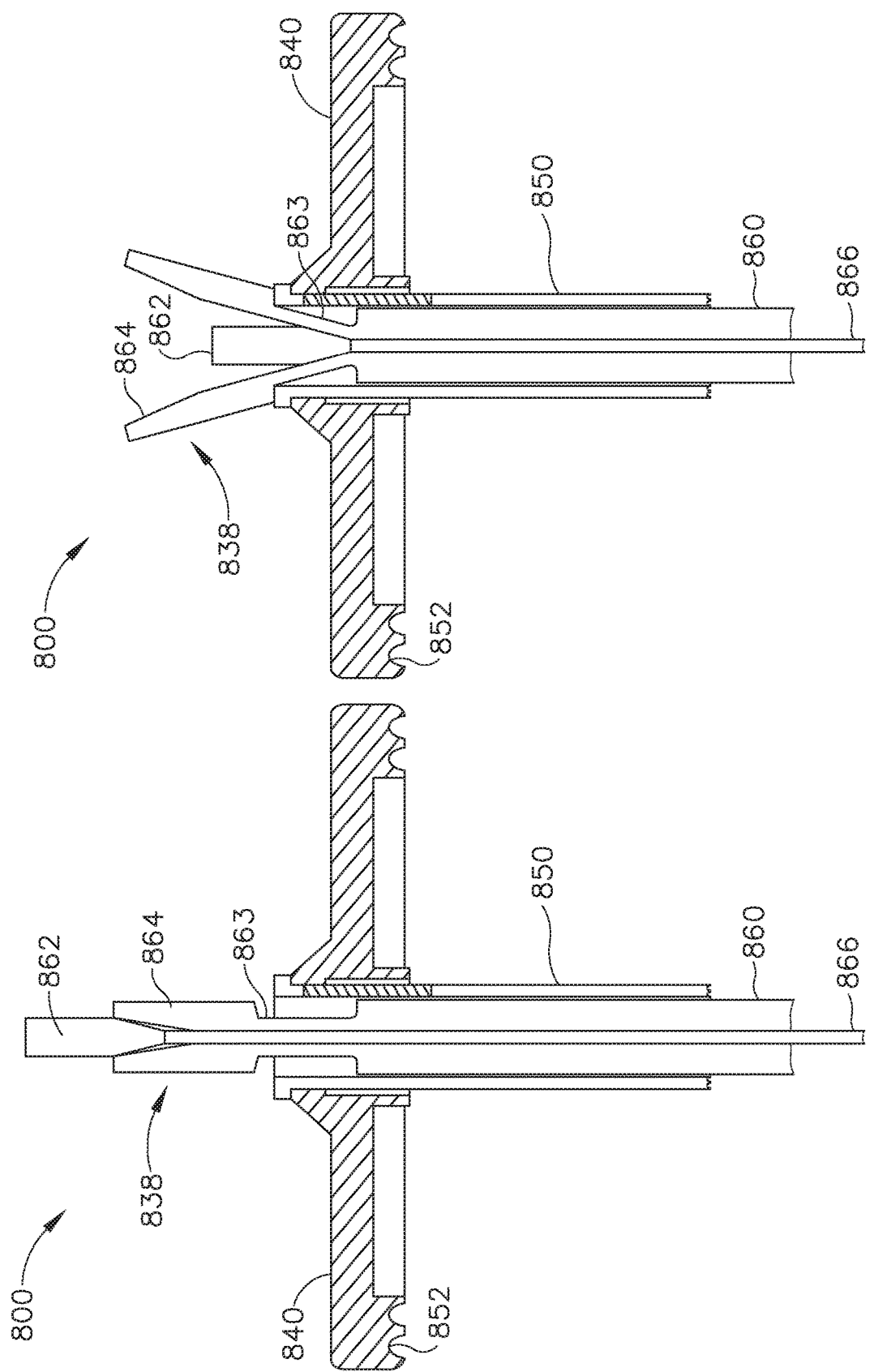
FIG. 24C depicts a cross sectional view of the anvil assembly and trocar of FIG. 24A showing the anvil coupled to the trocar with an anvil locking feature in a collapsed position.
FIG. 24D depicts a cross sectional view of the anvil assembly and trocar of FIG. 24A showing the anvil coupled to the trocar with the anvil locking feature in an expanded position.

Another exemplary anvil introduction system (800) is shown in FIGS. 24A-24D. Anvil introduction system (800) is similar to anvil introduction system (700), except that anvil introduction system (800) comprises an expanding trocar (838) to lock anvil (840) relative to trocar (838). Trocar (838) comprises a shaft (860) with recesses (863), an inner member (866) with a camming portion (862) at the distal end of inner member (866), and an expanding tip (864). Inner member (866) is positioned within shaft (860) and translatable relative to shaft (860). As described above, trocar (838) is inserted into anvil sleeve (850). As trocar (838) advances through sleeve (850), flexible section (848) bends to straighten sleeve (850) and align anvil (840) with stapling head assembly (20), as shown in FIG. 24B. A conventional grasper may be used to grasp anvil sleeve (850) to hold anvil sleeve (850) in place as trocar (838) is advanced through anvil sleeve (850). Trocar (838) advances through sleeve (850) until recess (863) is aligned above sleeve (850), as shown in FIG. 24C. Inner member (866) is then pulled or translated proximally. As inner member (866) slides proximally, camming portion (862) of inner member (866) pushes expanding tip (864) outward such that recesses (863) engage the top of sleeve (850) to lock anvil (840) relative to trocar (838). Inner member (866) may comprise a protrusion to align with an opening on shaft (860) to lock the longitudinal position of inner member (866) relative to shaft (860). Alternatively, any other suitable features may be used to selectively lock the longitudinal position of inner member (866) relative to shaft (860).

Another exemplary anvil introduction system (900) is shown in FIGS. 25A-27. Anvil introduction system (900) is similar to anvil introduction system (700), except that sleeve (950) comprises a plurality of rigid sections (948) along flexible sleeve (950). Anvil sleeve (950) is inserted through inner opening (943) of anvil (940). Sleeve (950) is formed from a compliant material and comprises a plurality of rigid sections (948), a first ring (982), a second ring (983), and openings (942). Rigid sections (948) are aligned along a side of sleeve (950) to allow sleeve (950) to bend about 180 degrees. Alternatively, sleeve (950) may be formed from a rigid material and comprise a plurality of flexible sections that are positioned along sleeve (950) and act as living hinges to allow sleeve (950) to bend. Other suitable configurations for rigid sections (948) will be apparent to one with ordinary skill in the art in view of the teachings herein. Rings (982, 983) are positioned at the ends of sleeve (950). Rings (982) are formed of a rigid material. Openings (942) are positioned adjacent to rings (982, 983). Sleeve (950) is configured such that either end of sleeve (950) may be attached to trocar (938). Trocar (938) comprises a shaft (960) extending from stapling head assembly (20), a tip (964) at the distal end of shaft (960), and tabs (968)

extending from shaft (960). Tabs (968) are configured to flex inward and align with openings (942) on sleeve (950).

As shown in FIG. 25A, sleeve (950) is inserted and wrapped around anvil (940). Jaws (946) of a grasper (947) are then used to grasp a ring (982) of sleeve (950) and pull anvil (940) down through a first severed esophagus section (2) to a desired anastomosis site. Grasper (947) may be used to pull a ring (982) of sleeve (950) through a portion of the first severed esophagus section. Trocar (938) and stapling head assembly (20) may be inserted up through a second severed esophagus section. Grasper (947) then slides ring (982) over trocar (938). As tip (964) of trocar (938) is inserted into sleeve (950), ring (982) flexes tabs inwardly until tabs (968) align with openings (942) of sleeve (950). Tabs (968) then flex outwardly through openings (942) to lock sleeve (950) relative to trocar (938), as shown in FIG. 25B. Grasper (947) may then be removed. Trocar (938) is then translated relative to stapling head assembly (20) to pull sleeve (950) within stapling head assembly (20). As sleeve (950) is translated proximally, flexible and rigid sections (948) of sleeve (950) slide through anvil (940) to straighten sleeve (950) and align anvil (940) with stapling head assembly (20), as shown in FIG. 25C. As trocar (938) continues to be retracted within stapling head assembly (20), anvil (940) slides along sleeve (950) until anvil (940) reaches ring (983) at the end of sleeve (950), as shown in FIG. 25D. Depending on which end of sleeve (950) is coupled to trocar (938), one of rings (982, 983) hold anvil (950) in place relative to trocar (938). Actuator (39) is then used to adjust the gap distance d between anvil (940) and trocar (938). Trigger (74) is actuated to drive stapling head assembly (20) to perform an anastomosis between the severed sections of the esophagus.

Figure 31:
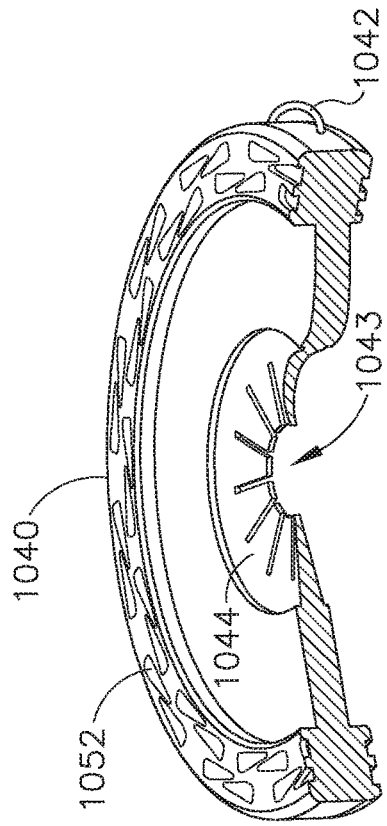
FIG. 31 depicts a top partial perspective view of the anvil of FIG. 28.
Figure 32:
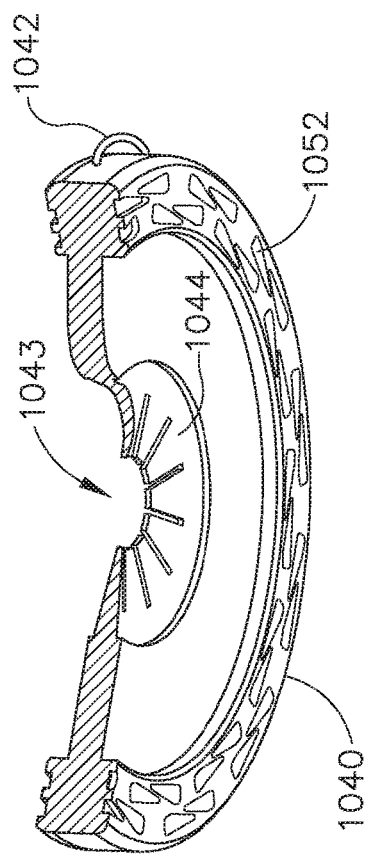
FIG. 32 depicts a bottom partial perspective view of the anvil of FIG. 28.
Figure 30:
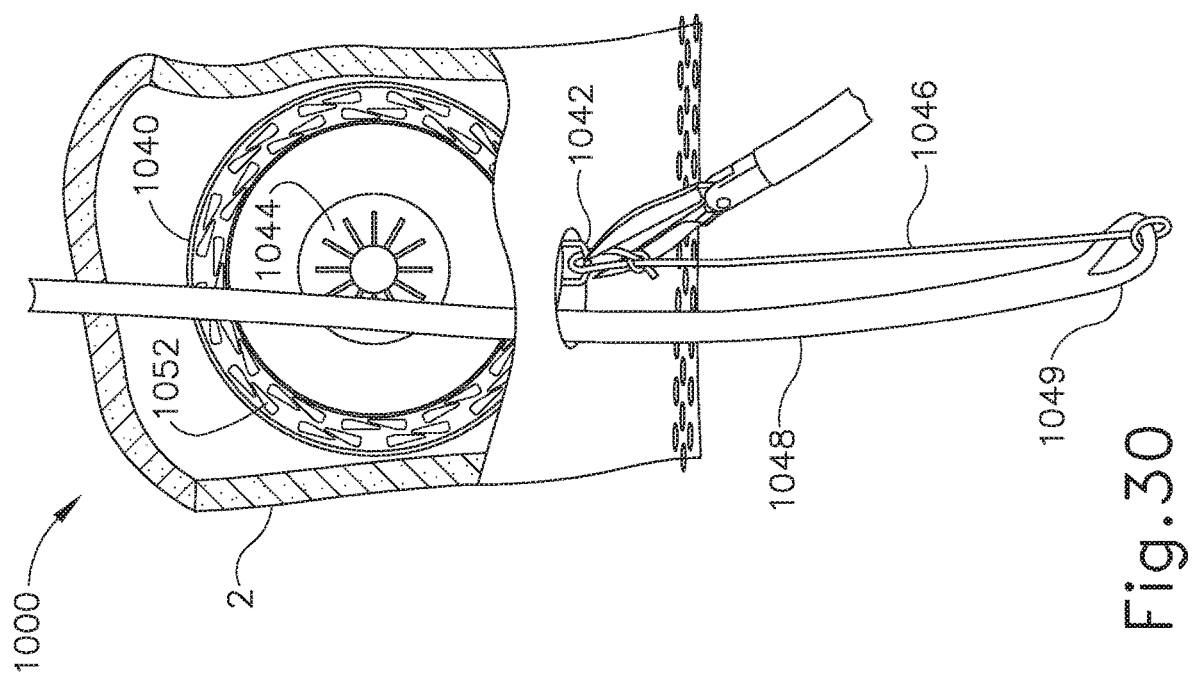
FIG. 30 depicts a partial perspective view of the instrument of FIG. 28 being removed from the anvil.

Alternatively, an anvil (1040) is introduced through a bodily lumen (e.g. the esophagus) with anvil introduction system (1000) shown in FIGS. 28-32. As shown in FIGS. 31-32, anvil (1040) comprises staple pockets (1052) aligned around both surfaces of disc-shaped anvil (1040). Anvil (1040) further comprises an inner opening (1043) and an integral loop (1042) extending from a side wall of anvil (1040). A suture (1046) is tied to loop (1042) of anvil (1040). The inner opening (1043) comprises flexible tabs (1044) to engage a trocar (38, 238, 338, 438, 538, 638, 738, 838, 938), similar to a spring nut. The other end of suture (1046) is tied to a loop (1049) of introduction member (1048). Introduction member (1048) is used to guide anvil (1040) through the esophagus to a desired stapling location. Introduction member (1048) may inserted trans-orally with anvil (1040) to pull anvil (1040) through the esophagus (FIG. 28). Alternatively, introduction member (1048) may be inserted through the stomach and up through the esophagus. Anvil (1040) may then be inserted trans-orally and coupled to introduction member (1048). Introduction member (1048) may then pull anvil (1040) back through the esophagus (FIG. 29). As shown in FIG. 30, when anvil (1040) is positioned the esophagus at a desired stapling location, suture (1046) is cut from loop (1042). Introduction member (1048) and suture (1046) are then removed from anvil (1040). Anvil (1040) is then aligned and coupled to a trocar (38, 238, 338, 438, 538, 638, 738, 838, 938).

Alternatively, an anvil (1140) may be introduced through a bodily lumen (e.g. the esophagus) with anvil introduction system (1100) shown in FIGS. 33A-33B. Anvil (1140) is similar to anvil (1040), except that anvil (1140) comprises a plurality of integral loops (1142). As shown, anvil (1140) comprises three loops (1142) evenly spaced around anvil (1140). However, a various amount of loops (1142) may be used and loops (1142) may be spaced asymmetrically around anvil (1140). Other suitable loop configurations will be apparent to one with ordinary skill in the art in view of the teachings herein. A suture (1146) is tied around each loop (1142). Sutures (1146) may comprise metal, plastic, or some other compliant member. Sutures (1146) are used to enable the control of the orientation of anvil (1140) within the esophagus. Although three sutures (1146) are shown, any suitable number of sutures (1146) may be used.

Anvil (1140) is inserted trans-orally through the esophagus in a vertical position. One of sutures (1146) may be used to pull anvil (1140) through the esophagus. Once anvil (1140) is pulled to a desired stapling location within the esophagus, the other two sutures (1146) are pulled to flip anvil (1140) to a horizontal position. All three sutures (1146) are then pulled against a wall of the esophagus to hold anvil (1140) in place. A trocar (38, 238, 338, 438, 538, 638, 738, 838, 938) is then coupled to anvil (1140) to perform an anastomosis.

D. Exemplary Washer

Figure 34:
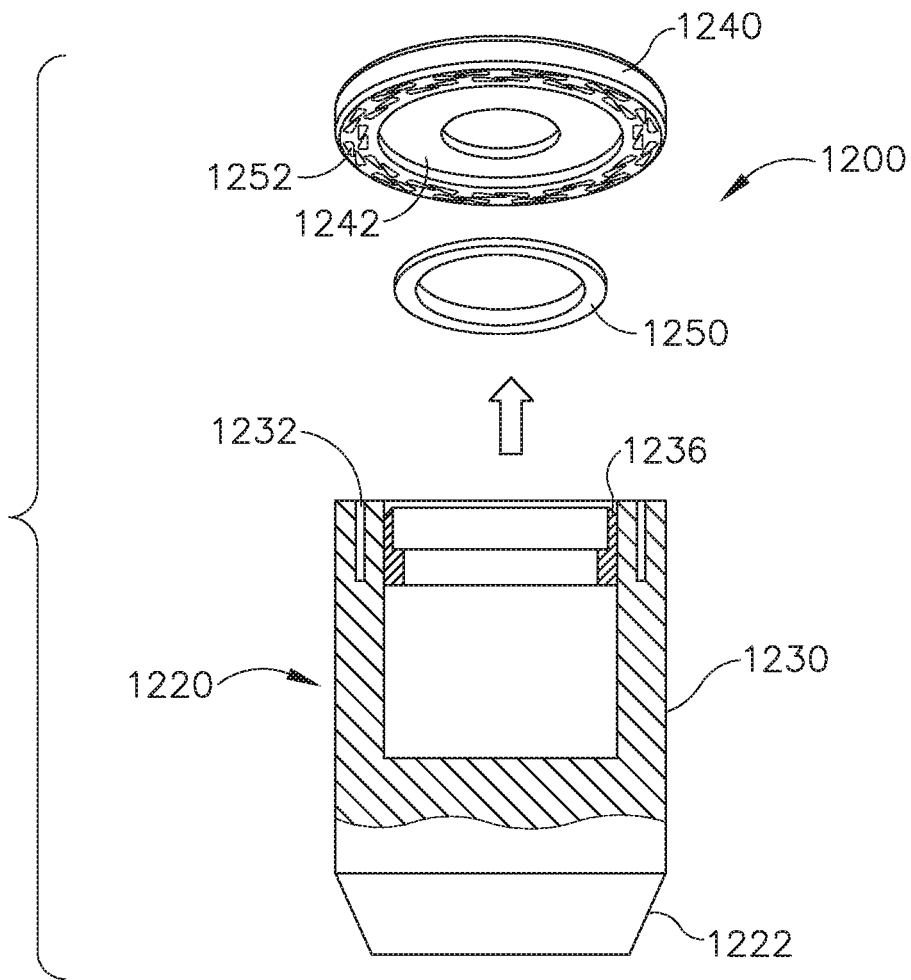
FIG. 34 depicts a partial perspective view of an exemplary anvil system.
Figure 35:
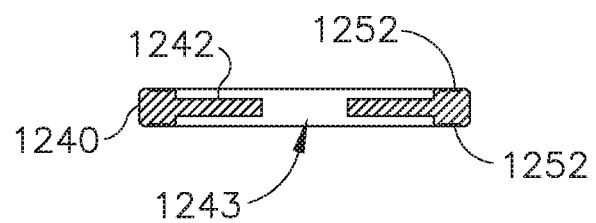
FIG. 35 depicts a cross sectional view of the anvil of FIG. 34.

During operation of stapling instrument (10), knife (36) may fracture a washer (1250) to provide audible feedback that stapling instrument (10) has fired. As shown in FIGS. 34-35, anvil (1240) comprises staple pockets (1252) aligned around both surfaces of disc-shaped anvil (1240). Anvil (1240) further comprises an inner wall (1242) that forms inner opening (1243). The configuration of anvil (1240) may be used in any of the configurations described above. Washer (1250) may be provided within stapling head assembly (1220) such that washer (1250) rests against knife (1236). The outer diameter of washer (1250) is sized to correspond to inner wall (1242) of anvil (1240) such that washer (1250) may engage inner wall (1242). As knife (1236) is fired, knife (1236) is configured to push washer (1250) against inner wall (1242) of anvil (1240) until knife (1236) fractures washer (1250) against anvil (1240).

Anvil (1240) may be inserted trans-orally through the esophagus as described above. Anvil (1240) is then coupled to a trocar (38, 238, 338, 438, 538, 638, 738, 838, 938) and stapling head assembly (1220). Actuator (39) is then used to adjust the gap between anvil (1240) and stapling head assembly (1220). Trigger (74) is actuated to drive stapling head assembly (20) to perform an anastomosis between the severed sections of the esophagus. When stapling instrument (10) is fired, knife (1236) pushes washer (1250) against inner wall (1242) of anvil (1240) and fractures washer (1250) to provide the audible feedback that stapling instrument (10) fired. Other suitable variations of washer (1250) and related features, as well as other suitable ways in which audible feedback may be provided, will be apparent to one with ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical. Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue, the apparatus comprising:
   (a) an anvil, wherein the anvil comprises:
      (i) a body, wherein the body has a disc shape,
      (ii) an inner opening formed through the body, and
      (iii) a plurality of staple pockets, wherein the plurality of staple pockets are positioned along a surface of the body;
   wherein the anvil is configured to be inserted through a bodily lumen;
   (b) a stapling head assembly defining a trocar opening; and
   (c) a trocar slidably disposed within the trocar opening of the staple head assembly, wherein the trocar is configured to selectively couple with the anvil, wherein the trocar comprises:
      (i) a shaft, and
      (ii) a locking assembly configured to transition from a collapsed position to an expanded position, wherein the locking assembly is operable to secure the anvil in position relative to the shaft of the trocar when the locking assembly is in the expanded position, wherein the locking assembly comprises an expanding member configured to engage the anvil when the locking assembly is in the expanded position, wherein the expanding member comprises a recess configured to engage a wall of the inner opening of the anvil when the locking assembly is in the expanded position.

2. The apparatus of claim 1, wherein the anvil comprises a first plurality of staple pockets positioned along a top surface and a second plurality of staple pockets positioned along a bottom surface of the body.

3. The apparatus of claim 1, wherein the locking assembly comprises at least one resilient tab extending from the shaft of the trocar.

4. The apparatus of claim 3, wherein the locking assembly comprises a pair of resilient tabs extending from the shaft of the trocar.

5. The apparatus of claim 3, wherein the tab is resiliently biased by a resilient member.

6. The apparatus of claim 3, wherein the at least one tab is configured to engage a top surface of the anvil when the locking assembly is in the expanded position.

7. The apparatus of claim 6, wherein the anvil further comprises a sleeve extending from the anvil, wherein the sleeve comprises at least one opening, wherein the at least one tab is configured to engage the at least one opening when the locking assembly is in the expanded position.

8. The apparatus of claim 7, wherein the sleeve is configured to extend through the inner opening of the anvil, wherein the sleeve comprises at least one opening adjacent to a first end of the sleeve and at least one opening adjacent to a second end of the sleeve, such that the sleeve is configured to couple either the first end or the second end of the sleeve with the trocar.

9. The apparatus of claim 8, wherein the sleeve comprises a flexible section.

10. The apparatus of claim 1, wherein the locking assembly further comprises a camming member, wherein the camming member is translatable within the shaft of the trocar, wherein the camming member is operable to move the locking assembly from the collapsed position to the expanded position.

11. The apparatus of claim 10, wherein the trocar further comprises at least one fin configured to engage a bottom surface of the anvil.

12. The apparatus of claim 11, wherein the at least one fin is operable to lock the camming member relative to the shaft of the trocar.

13. The apparatus of claim 1, wherein the locking assembly comprises an inner member translatable relative to the shaft of the trocar, a first expanding member secured to the inner member, and a second expanding member coupled to the first expanding member and secured to the shaft of the trocar.

14. An apparatus for stapling tissue, the apparatus comprising:
 (a) an anvil configured to be inserted through a bodily lumen, wherein the anvil comprises:
  (i) a body, wherein the body defines an inner opening, and
  (ii) a surface defining an annular array of staple forming pockets;
 (b) a stapling head assembly defining a trocar opening, wherein the staple head assembly is configured to drive an annular array of staples into the annular array of staple forming pockets;
 (c) a trocar actuation assembly; and
 (d) a trocar slidably coupled with the stapling head assembly, wherein the trocar actuation assembly is configured to drive translation of the trocar through the trocar opening defined by the stapling head assembly, wherein the trocar is selectively coupled with the anvil, wherein the trocar, when selectively coupled with the anvil and translated by the trocar actuation assembly, is configured to drive the anvil relative to the staple head assembly to define a gap between the anvil and the staple head assembly, wherein the trocar comprises:
  (i) a shaft defining an interior recess, and
  (ii) a locking assembly comprising and actuating arm slidable housed within the interior recess, and an engagement body configured to transition between a first position and a second position relative to the shaft in response to the actuating arm sliding relative to the shaft, wherein the engagement body, while in the first position, is dimensioned to fit within the inner opening of the body of the anvil such that the trocar is configured to actuate relative to the anvil while the engagement body is in the first position, wherein the engagement body, while in the second position, is configured to attach to the anvil such that the trocar is configured to actuate the anvil relative to the staple head assembly when the engagement body is in the second position.

15. The apparatus of claim 14, wherein the actuating arm is resiliently biased toward a proximal direction.

16. The apparatus of claim 15, further comprising a release body pivotally coupled to the shaft, wherein the release body is configured to contact the anvil to allow the actuating arm to translate toward the proximal direction.

17. The apparatus of claim 14, further comprising a camming member configured to allow the actuating body to translate within the interior recess of the shaft.

18. An apparatus for stapling tissue, the apparatus comprising:
 (a) an anvil configured to be inserted through a bodily lumen, wherein the anvil comprises:
  (i) a body, wherein the body defines an inner opening, and
  (ii) a surface defining an annular array of staple forming pockets;
 (b) a stapling head assembly configured to drive an annular array of staples in into the annular array of staple forming pockets, wherein the stapling head assembly defines a trocar opening;
 (c) a trocar actuation assembly; and
 (d) a trocar slidably disposed within the trocar opening of the stapling head assembly, wherein the trocar actuation assembly is configured to actuate the trocar relative to the staple head assembly, wherein the trocar is configured to selectively couple with the anvil, wherein the anvil and the stapling head assembly define a gap distance when the anvil is coupled to the trocar, wherein the trocar comprises:
  (i) a shaft defining an interior recess, and
  (ii) a locking assembly comprising a locking body, and an engagement body configured to transition between a first position and a second position, wherein the engagement body is dimensioned to actuate within the inner opening of the body of the anvil when the engagement body is in the first position, wherein the engagement body is configured to attach to the anvil when the engagement body is in the second position, wherein the locking body is configured to selectively prevent the engagement body from transition from the first position to the second position.

* * * * *